(12) United States Patent
Rozenszain et al.

(10) Patent No.: US 9,155,323 B2
(45) Date of Patent: Oct. 13, 2015

(54) AQUEOUS PROCESS FOR PREPARING PROTEIN ISOLATE AND HYDROLYZED PROTEIN FROM AN OILSEED

(75) Inventors: Luis Rozenszain, Burlington (CA); Garrison Beye, Clayton (CA)

(73) Assignee: SIEBTE PMI VERWALTUNGS GMBH, Hamburg (DE)

( * ) Notice: Subject to any disclaimer, the term of this patent is extended or adjusted under 35 U.S.C. 154(b) by 18 days.

(21) Appl. No.: 13/438,709

(22) Filed: Apr. 3, 2012

(65) Prior Publication Data

US 2012/0252065 A1 Oct. 4, 2012

Related U.S. Application Data

(63) Continuation-in-part of application No. 12/927,299, filed on Nov. 10, 2010, which is a continuation-in-part of application No. 12/927,313, filed on Nov. 10, 2010, which is a continuation-in-part of application No. 12/616,375, filed on Nov. 11, 2009, which is a continuation-in-part of application No. 12/467,227, filed on May 15, 2009.

(60) Provisional application No. 61/471,679, filed on Apr. 4, 2011, provisional application No. 61/553,898, filed on Oct. 31, 2011.

(51) Int. Cl.
| | | |
|---|---|---|
| *A23J 1/14* | (2006.01) | |
| *A23J 3/00* | (2006.01) | |
| *C12P 13/04* | (2006.01) | |
| *C12P 21/06* | (2006.01) | |
| *A23J 3/34* | (2006.01) | |

(52) U.S. Cl.
CPC .. *A23J 1/14* (2013.01); *A23J 3/346* (2013.01); *C12P 13/04* (2013.01); *C12P 21/06* (2013.01)

(58) Field of Classification Search
CPC ............. A23J 1/14; A23J 3/346; C12P 21/06; C12P 13/04
USPC .................. 435/68.1; 530/377, 378, 402, 422
See application file for complete search history.

(56) References Cited

U.S. PATENT DOCUMENTS

| | | | | |
|---|---|---|---|---|
| 2,353,011 | A * | 7/1944 | Buxton | 424/554 |
| 3,579,496 | A * | 5/1971 | Martinez et al. | 530/377 |
| 3,640,725 | A | 2/1972 | Sherba et al. | |
| 3,732,108 | A | 5/1973 | Eapen et al. | |
| 3,736,147 | A | 5/1973 | Iaobucci | |
| 3,809,771 | A | 5/1974 | Mustakas | |
| 3,816,389 | A | 6/1974 | Mihara et al. | |
| 3,865,802 | A | 2/1975 | Mustakas | |
| 3,966,971 | A | 6/1976 | Morehouse | |
| 4,039,696 | A * | 8/1977 | Marquardt et al. | 426/598 |
| 4,420,425 | A | 12/1983 | Lawhon | |
| 4,859,371 | A | 8/1989 | Diosady et al. | |
| 4,889,921 | A * | 12/1989 | Diosady et al. | 530/377 |
| 6,653,087 | B1 | 11/2003 | Boger | |
| 6,660,167 | B1 | 12/2003 | Walder et al. | |
| 6,998,466 | B2 * | 2/2006 | Nennerfelt et al. | 530/344 |
| 7,083,948 | B1 | 8/2006 | Sassenfeld et al. | |
| 7,122,216 | B2 * | 10/2006 | Copeland et al. | 426/417 |
| 7,156,981 | B2 | 1/2007 | Wilde et al. | |
| 7,429,399 | B2 | 9/2008 | Porter et al. | |
| 2004/0034200 | A1 * | 2/2004 | Logie et al. | 530/377 |
| 2009/0036655 | A1 | 2/2009 | Segall | |
| 2009/0286961 | A1 * | 11/2009 | Tang | 530/377 |
| 2010/0040748 | A1 | 2/2010 | Maenz | |
| 2010/0234569 | A1 | 9/2010 | Helling et al. | |

FOREIGN PATENT DOCUMENTS

| | | |
|---|---|---|
| CA | 2244398 | 1/1997 |
| CA | 2751608 | 8/2010 |
| WO | WO 95/27406 | * 10/1995 |
| WO | WO2009/137934 | 11/2009 |

OTHER PUBLICATIONS

Newkirk Rw and Classen HL (1998). In vitro hydrolysis of phytate in canola meal with purified and crude sources of phytase. Animal Feed Science and Technology, v72, p. 315-327.*

Prior EM et al. (1991). Effect of Heat Treatments on Canola Press Oils. I. Non-triglyceride components. JOACS, v68(6), p. 401-406.*

Zhang SB et al. (2007). Optimization of the Aqueous Enzymatic Extraction of Rapeseed Oil and Protein Hydrolysates. JAOCS, v84, p. 97-105.*

Prior EM et al. (1991). Effect of Heat Treatments on Canola Press Oils. JAOCS, v68(6), p. 401-406.*

Spellman D et al. (2005). Aggregation of Properties of Whey Protein Hydrolysates Generated with Bacillus licheniformis Proteinase Activities. J Agric Food Chem, v53, p. 1258-1265.*

(Continued)

*Primary Examiner* — Sharmila G. Landau
*Assistant Examiner* — Sean C Barron
(74) *Attorney, Agent, or Firm* — Koppel, Patrick, Heybl & Philpott; Michael J. Ram

(57) ABSTRACT

Disclosed is an aqueous process for the preparation of a protein isolate and a hydrolyzed protein concentrate from an oilseed meal, comprising: 1) mixing an oilseed meal with an aqueous solvent to form a slurry; 1a) optionally treating the slurry with phytase; 2) separating the slurry with a solid/liquid separation to form a liquid phase comprising the aqueous solvent, soluble protein and oil; and a solid phase comprising insoluble protein; 3) separating the liquid phase to form an oil phase and an aqueous protein phase; 4) subjecting the aqueous protein phase to membrane filtration to obtain a protein solution and drying the protein solution to obtain the protein isolate, subjecting the insoluble protein to enzymatic hydrolysis, and 5) subjecting the hydrolyzed protein to membrane filtration to obtain an amino acid and peptide solution; and drying the amino acid and peptide solution to obtain the hydrolyzed protein concentrate.

46 Claims, 8 Drawing Sheets

(56) References Cited

OTHER PUBLICATIONS

Ghorbel B et al. (2003). Stability studies of protease from Bacillus cereus BG1. Enzyme and Microbial Technology, v32, p. 513-518.*

Sosulski F et al. (1981) Fractionation of Rapeseed meal into Flour and Hull Components. JAOCS, v58(6), p. 96-98.*

McLennan PL et al. (1995). Dietary canola oil modifies myocardial fatty acids and inhibits cardiac arrhythmias in rats. The Journal of Nutrition, v125(4), p. 1003-1009.*

Rapeseed. (2005). In Dictionary of Food: International Food and Cooking Terms from A to Z. Retrieved from http://www.credoreference.com/entry/acbdictfood/rapeseed.*

Sadeghi et al. (2006). Evaluation of mustard (Brassica juncea) protein isolate prepared by steam injection heating for reduction of antinutritional factors. LWT, v39, p. 911-917.*

Newkirk et al. (1998). In vitro hydrolysis of phytate in canola meal with purified and crude sources of phytase. Animal Science and Feed Technology, v72, p. 315-327.*

Sarmento, M.J. et al., Liquid-Liquid Extraction of a Recombinant Protein, Cytochrome b5 from an impure extract using aqueous two-phase systems. Bioprocess and Biosystems Engineering 16(5):295-297. 1997.

Cater, C.M. et al. Aqueous Extraction—An Alternative Oilseed Milling Process. J. Am. Oil Chem. Soc. 51(4): 137-141, 1973.

Thobani, M. And Diosady, L.L. Two-phas Solvent Extraction of Canola. Journal of the American Oils Chemists' Society. 74(3):207-2141, 1997.

Pires MJ and Cabral JM. Liquid—Liquid Extraction of a Recombinant Protein with a Reverse Micelle Phase, Biotechnol. Prog. 9(6):647-650. 1993.

Dhananjay Dendukuri and Levente L. Diosady. Oil-Free Protein Isolates from Full-Fat, Dehulled Mustard Flour by Microfiltration. JAOCS, 80(3):287-294 (2003).

Campbell, K.A. et al., Advances in Aqueous Extraction Processing of Soybeans. J. Am. Oil Chem. Soc. 88:449-465, 2011.

Balke, David Thomas. Thesis. Aqueous Extration of Protein and Oil from Mustard Flour. Production of Higher Value Ingredients from White Mustard Seed Via Aqueous Extraction, p. 88-98, 2006.

Extended Search Report, European Patent Application No. 12767675, issued Jul. 28, 2014.

Lisa K. Karr-Lilienthal et al., "Amino Acid, Carbohydrate, and Fat Composition of Soybean Meals Prepared at 55 Commercial U.S. Soybean Processing Plants", *Journal of Agricultural and Food Chemistry*, vol. 53, No. 6, (Mar. 1, 2005), pp. 2146-2150, XP055129549, ISSN: 0021-8561, DOI: 10.1021/jf048385i.

* cited by examiner

PROTEIN ISOLATES PROCESS FLOW DIAGRAM WITH MF

US 9,155,323 B2

AQUEOUS PROCESS FOR PREPARING PROTEIN ISOLATE AND HYDROLYZED PROTEIN FROM AN OILSEED

PRIORITY INFORMATION

This application claims the benefit of U.S. Provisional Application No. 61/471,679 filed Apr. 4, 2011, U.S. Provisional Application No. 61/553,898 filed Oct. 31, 2011, U.S. patent application Ser. No. 12/927,299 filed Nov. 10, 2010, U.S. patent application Ser. No. 12/927,313 filed Nov. 10, 2010, U.S. patent application Ser. No. 12/616,375 filed Nov. 11, 2009, and U.S. patent application Ser. No. 12/467,227 filed May 15, 2009.

FIELD OF THE DISCLOSURE

This application relates to an aqueous process for preparing a soluble protein product, referred to as an isolate, from an oilseed and a composition comprising soluble amino acids and peptides by the hydrolysis of insoluble protein recovered in the process of forming the isolate. In particular the process results in the isolation of superior, high purity, proteins from oilseed, the product having a significant increase in absorbable protein over that available from using prior oil removal and protein recovery procedures.

BACKGROUND OF THE DISCLOSURE

Oilseeds generally contain from about 20% to about 50% oil by weight with the percentages varying with the type of oilseed. Often, oilseed meals are pressed to remove the majority of oil. However, even with pressing, a significant amount of oil remains in the meal. Oil content of the meal can be reduced to about 10-25% by mechanical processing (pressing) and then further processed using various solvents to reduce the oil content to about 3%. The pressed oilseed meal is generally removed using low-boiling organic solvents such as hexane. While these organic solvents can remove additional oil from the oil seed meals by extraction, the use of such organic solvents, even though they may be relatively low boiling, still require elevated temperatures for solvent removal. Elevated temperatures can result in denaturing of the protein, which degrades soluble protein resulting in increased levels of insoluble protein thereby reducing the nutritional value of the product. The use of solvent (other than water) results in environmental issues, as well as recovery and disposal problems in addition to increased energy usage. Even when elevated temperatures are used, residual organic solvent is trapped within the solvent-extracted meal; this residual solvent is difficult to remove without denaturing the protein in the meal.

U.S. Pat. No. 7,156,981 describes the use of an extraction solvent that has an even lower boiling point than hexane. Iodotrifluoromethane ($CIF_3$, also referred to herein as ITFM) alone or with cosolvents, such as HFC-134 can be used at ambient temperature or below with elevated pressures sufficient to keep the solvent in a liquid state, avoiding the need for elevated temperatures and thus significantly reducing the denaturing of the protein. However, because of the need for elevated pressures, the quantity of HTFM required for suitable extraction, high costs of the HTFM and environmental concerns, a more suitable alternative to hexane, HTFM or other extraction techniques is desired.

SUMMARY OF THE DISCLOSURE

Disclosed herein is an aqueous process for the preparation of soluble protein products, such as a protein isolate. As set forth herein, the oil seed does not require the use of solvents to provide a meal sufficiently reduced in oil content suitable for further processing. That oilseed meal can then be further processed without the use of a solvent other than an aqueous solution, preferably only water. In other words, the only solvent used in the process, starting from seed crushing to final protein recovery is an aqueous solution, preferably just water (for example, tap water, city water, or any other source of potable water) and more preferably RO (reverse osmosis) water. Accordingly, the protein products (such as protein isolates) do not suffer from contamination of organic solvents, salts or other extraction media. Various embodiments result in protein isolates with high concentrations of soluble protein (>90%) containing less than 2% (w/w) of oil.

Accordingly, the disclosure includes a process for preparing a protein isolate from an oilseed, comprising:

crushing, milling, or otherwise mechanically processing, without the use of any solvent, the oil seed to provide an oil seed meal having an oil content of about 12-18% oil;

mixing the oilseed meal with an aqueous solvent, preferably water, to form a slurry;

optionally treating the slurry with phytase at a temperature and a pH suitable for phytase activity;

optionally adjusting the pH of the slurry to improve the solubility of the soluble protein and to optionally obtain a pH neutral solution, optionally to a pH of between 6.5 and 7.5, optionally 7.0;

separating the slurry into:
a liquid phase, comprising the aqueous solvent, soluble protein and oil; and
a solid phase;
separating the liquid phase to form
an oil phase and
an aqueous protein phase;

separating the aqueous protein phase, preferably by membrane filtration, to separate a protein solution and undissolved material from sugars, ash, and other low molecular weight impurities; and drying the protein solution to obtain an isolate comprising a high concentration of water soluble protein.

In another embodiment insoluble protein separated and recovered in the process of preparing the soluble protein isolate is hydrolyzed using enzymes to produce a product comprising soluble amino acids and peptides.

In another embodiment, the process further comprises mixing the solid phase with an aqueous solvent and repeating the solid/liquid separation from one to four times to recover further soluble protein.

In a further embodiment, the ratio of the oilseed meal to the aqueous solvent is between 1:5 and 1:15 (w/w) of meal to solvent, or from about 1:8 to 1:15 (w/w) of meal to solvent, or about 1:8 to 1:12.5.

In another embodiment, the temperature suitable for phytase activity is between 20° C. and 65° C. and the pH suitable for phytase activity is between 4.5 and 7.5; preferably the temperature suitable for phytase activity is about 50° C. and the pH suitable for phytase activity is between 4.8-5.2.

In a further embodiment, the separation of the solids from the liquid is conducted by centrifugation, optionally by a decanter centrifuge. In preferred embodiment, a decanter centrifuge is operated at a g-force of between 2,000-4,000 g. In a preferred embodiment, the g-force is about 2500-4000. In one embodiment, the decanting centrifuge is operated at a temperature of between 10° C. and 20° C., or less than about 20° C. but greater than about 0° C., or about 20° C.

In another embodiment, the separation of the liquid phase can be conducted by centrifugation, for example by use of a skimming centrifuge, a 2-phase centrifuge, a 3-phase centrifuge, by two 2-phase centrifuges in sequence or similar arrangements. The centrifuge can be operated at a g-force of between 2,000-14,000 g optionally at a g-force of between 2,900-14,000 g.

In another embodiment, the aqueous protein phase is subjected to, microfiltration (and diafiltration), ultrafiltration and/or ultrafiltration followed by diafiltration to recover a purified protein solution.

As used herein in a preferred embodiment the aqueous solvent comprises water, which can be tap water, distilled water or preferably water processed using reverse osmosis (RO).

In a further embodiment, the process can be a batch process, a semi-continuous process, a continuous process or any combination thereof.

In an embodiment, the protein isolate comprises less than 2% (w/w) oil. In a further embodiment, the protein isolate comprises at least 90% (w/w) on a dry weight basis.

While the process herein is described for processing canola seed and canola meal, other oil seeds, including, but not limited to, rapeseed, mustard seed, broccoli seed, flax seed, cotton seed, hemp seed, safflower seed, sesame seed and soybean meal, can be processed in the same manner to provide high protein content end products. Further, while the process described starts with canola oil seed, it is contemplated that any other source of canola oil seed meal can be processed as set forth herein to provide a high protein content end product.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE FIGURES

Embodiments of the disclosure will be described in relation to the drawings in which.

DETAILED DESCRIPTION

Definitions

Figure 1:
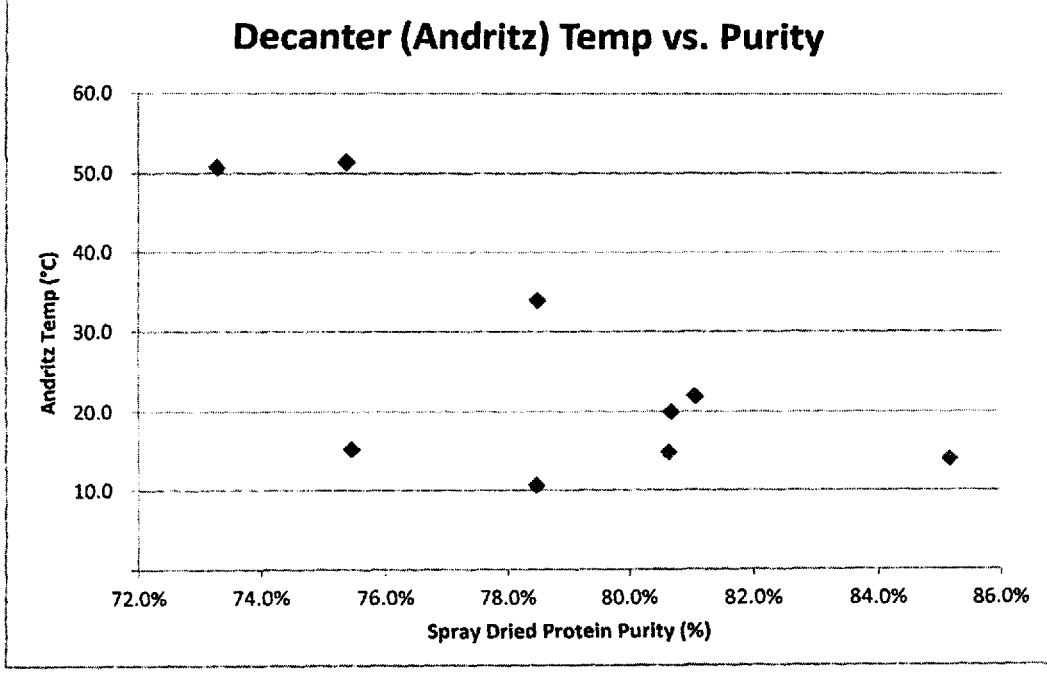
FIG. 1 is a graph demonstrating the relationship between the purity of the a spray dried protein and the temperature during decanter centrifugation.

The term "oilseed meal" as used herein refers to a meal prepared from an oilseed in which the oilseed has been ground and crushed to form a meal and from which no oil has been removed; or optionally the oilseed has been pressed to remove the oil contained within to form a meal referred to as a "pressed cake" or a "partially defatted meal". Optionally, the meal can be pressed to remove oil leaving a presscake with a reduced oil content. The oil seed, or optionally the seed cake, can be subjected to solvent extraction, using, for example, hydrophobic solvents such as pentane, hexane and/or other refrigerants such as iodotrifluoromethane (ITFM) and R134a (1,1,1,2-tetrafluoroethane), to remove or reduce residual oil from the seedcake and form a "defatted meal". The pressing of the oilseed results in pressed oil and a partially defatted meal, which contains from about 15% to about 50% of protein on a dry weight basis and from about 10% to about 20% oil, optionally about 14% to 16%, on a dry weight basis. A defatted meal (which has been solvent extracted) will typically have a protein content of about 25% to about 55%, optionally 30% to about 50%, suitably about 35% to about 50%, on a dry weight basis. The oil seed prior to pressing has an oil content of 40%-50% and after about 0.5% to about 4%, optionally about 1% to about 3%, on a dry weight basis.

The term "aqueous solvent" as used herein refers to any solvent in which water comprises the majority of the solvent (typically from about 80%, to 99.9% water by weight), or pure water. The aqueous solvent optionally comprises, consisting essentially of, or consisting of water. While the pure water may comprise tap water it preferably comprises processed water, such as deionized, distilled water or RO water (water subjected to reverse osmosis treatment), acidic water, or alkaline water with no organic solvent or added salt present. An exception may be the addition of small amounts of acidic, basic or buffer compounds for adjusting pH. The aqueous solvent forms a slurry and/or mixture when contacted with an oilseed meal. Typically the aqueous solvent is free from organic solvents, such as methanol, propanol, isopropanol, tetrahydrofuran, etc., since these solvents are not desirable as residues in a protein product for human consumption. However, if organic solvents are present, for example, ethanol, they form part of the aqueous solvent in small amounts (e.g., typically equal to or less than 20%, 15%, 10%, 5%, 2% or 1%) so that their presence in the final product can be reduced to an acceptable or negligible amount. A person skilled in the art would understand that tap water, can contain natural minerals, salts and/or other solutes, which would not affect the process of the disclosure.

The term "protein isolate" as used herein refers to an oilseed meal that has been treated using the processes of the present disclosure to increase the protein content, where the protein isolate has a high soluble protein content greater than about 85%, but preferably 90% or greater than 90% protein on a dry weight basis. The balance may comprise carbohydrate, ash, and oil.

The term "slurry" as used herein refers to the oilseed meal that has been mixed with an aqueous solvent to form a liquid containing dissolved protein and a suspension of protein, oil and optionally fiber and anti-nutritional compounds, in the liquid.

The term "suitable for phytase activity" as used herein refers to the conditions, such as the temperature and pH, and optionally includes the length of time, in which the phytase enzyme is able to hydrolyze the phosphate groups on phytate or phytic acid so as to reduce the amount of phytates or phytic acid in the mixture. In an embodiment, the temperature suitable for phytase activity is between 20° C. and 65° C., optionally between 40° C. and 55° C., more suitably between 50° C. and 55° C. In another embodiment, the pH suitable for phytase activity is between 2.0 and 7.0, optionally between 4.0 and 6.0, more suitably between 4.8 and 5.2 or optionally 5.0 to 5.5. In another embodiment, the concentration of the phytase enzyme is below about 2% (w/w) based on the weight of the oilseed meal, and optionally 0.5%-1.5% or 1.0-1.5% and may be as low as 0.01% and 0.1%, depending on the phytic acid concentration in the meal. It will be understood that the conditions suitable for phytase activity apply to all of the processes of the present disclosure.

The term "liquid phase" as used herein refers to the aqueous solvent of the slurry in which soluble protein from the oilseed meal has been dissolved, along with other solubles such as ash, minerals, etc. In addition, a portion of the oil present in the oilseed meal can be present in the aqueous solvent during the separation process.

The term "solid phase" as used herein refers to insoluble compounds, such as insoluble protein, fibre and oil which are not soluble in the aqueous solvent, and form a solids phase, which can contain liquid oil, upon separation.

The phrase "separating the slurry with a solid/liquid separation" as used herein refers to any solid/liquid separation process which is able to separate the slurry into a solid phase and a liquid phase. For example, the use of a centrifuge, such as a decanter centrifuge, pressing, such as using a screw press, filter press, belt press, French press, etc, settling, or any other means that separates the slurry into a solid phase and a liquid phase. One skilled in the art will be aware of various different techniques, procedures and equipment that can be suitable for separating liquids from the solids, or any other means that separate the slurry into a solid phase and a liquid phase.

The phrase "separating the liquid phase" as used herein refers to any process which is able to separate two liquids having different densities or solubilities, such as for example a 3 phase centrifuge, which is able to separate the oil and the aqueous protein phase in the liquid phase (i.e., 2 phases having dissimilar densities).

Terms of degree such as "substantially", "about" and "approximately" as used herein mean a reasonable amount of deviation of the modified term such that the end result is not significantly changed. These terms of degree should be construed as including a deviation of at least ±10% of the modified term if this deviation would not negate the meaning of the word it modifies.

Processes Incorporating Features of the Invention

The present disclosure relates to an aqueous process for the preparation of a protein isolate. In one embodiment, when the meal is added to the aqueous solvent, the oil from the oilseed meal is separated from the soluble protein and principally is separated therefrom with the solids phase. In a further embodiment, protein extraction of the soluble protein by the aqueous solvent is relatively unaffected by the presence of some of the oil which may be carried along with the aqueous solvent. In another embodiment, oil which remains with the aqueous solvent in the process of the present disclosure floats on the surface of the aqueous solvent after a separation process, for example by centrifugation, and is then removed using the separation processes of the present disclosure.

Accordingly, in one embodiment of the disclosure, the protein isolates contain less than 2% (w/w) of oil.

Accordingly, the disclosure includes a process for preparing a protein isolate from an oilseed meal, comprising a process including at least some of the following steps:
    pressing an oil seed to remove a portion of the oil to form an oilseed meal or a partially defatted meal;
    mixing the oilseed meal or partially defatted meal with an aqueous solvent to form a mixture;
    optionally treating the mixture with phytase at a temperature and a pH suitable for phytase activity for a period of time to enzymatically reduce the phytate concentration;
    optionally adjusting the pH of the slurry to improve the solubility of the soluble protein and to optionally obtain a pH neutral solution, optionally to a pH of between 6.5 and 7.5, optionally 7.0,
    separating the mixture with a solid/liquid separation to form:
        a liquid phase, comprising the aqueous solvent, soluble protein and oil; and
        a solid phase;
    separating the liquid phase to form:
        an oil phase; and
        an aqueous protein phase;
    subjecting the aqueous protein phase to filtration to obtain a protein solution; and drying the protein solution to obtain the protein isolate.

In another embodiment, the liquid phase also comprises residual solids (fines) which are removed using a polishing centrifuge, a 2-phase centrifuge or other suitable filtering or screening techniques.

In another embodiment, the process further comprises mixing the solid phase with an aqueous solvent and repeating the solid/liquid separation from one to four times to recover more soluble protein.

In a further embodiment, the ratio of the oilseed meal to the aqueous solvent is between 1:5 and 1:15 (w/w) of meal to solvent, or from about 1:8 to 1:15 (w/w) of meal to solvent, or about 1:8 to 1:12.5.

In another embodiment, the temperature suitable for phytase activity is between 20° C. and 65° C. and the pH suitable for phytase activity is between 4.5 and 7.5, optionally the temperature suitable for phytase activity is 50° C.±5° C. and the pH suitable for phytase activity is between about 4.8-5.2.

In a further embodiment, the solid liquid separation is conducted by centrifugation, optionally by a decanter centrifuge. In another embodiment, the decanter centrifuge is operated at a g-force between 2,000-4,000 g, preferably between 3,000-4000 g. However, other techniques discussed herein, such as filtering or pressing can be alternatively used. Also, dewatering using rotational or stationary dewatering screens or filters followed by pressing could also be used to for the solid liquid separation. When the solid liquid separation is conducted using a decanter centrifuge, a liquid phase is obtained, and the liquid phase optionally contains residual insolubles or solids, such as residual insoluble proteins. In one embodiment, the liquid phase containing residual solids is further subjected to centrifugation using a disk stack centrifuge, and optionally two disk stack centrifuges in series. In one embodiment, the first disk stack centrifuge is operated at a g-force between 6,000-9,000 g, optionally between 8,000 g-9,000 g, and the second disk stack centrifuge is operated at a g-force between 8,000 g-12,000 g, optionally 10,000 g. In an embodiment, the separation of the liquid phase is conducted by centrifugation. In another embodiment, the separation of the component parts of the liquid phase is conducted by using, for example, a skimming centrifuge, a 2-phase centrifuge or a 3-phase centrifuge. In one embodiment, the two-phase centrifuge is a disk stack centrifuge. In an embodiment, the separation of the liquid phase is conducted by two 2-phase centrifuges in sequence. In another embodiment of the disclosure, the centrifuge is operated at a g-force between 2,000-14,000 g, optionally at a g-force of between 2,900-14,000 g, optionally 6,000 g. It should be recognized that these are examples of suggested operating conditions and the composition of the liquid to be separated can necessitate operating at different condition or using separation techniques other than a centrifuge to separate solids from liquids or two immiscible liquid phases.

In another embodiment, the aqueous protein phase is subjected to one or more steps of microfiltration, ultrafiltration and/or by diafiltration, not necessarily in that order, to obtain a retentate comprising a protein solution.

In a preferred embodiment of the disclosure, the aqueous solvent comprises or consists of water. However, the aqueous solvent can comprises a saline solution such as sodium chloride, potassium chloride, calcium chloride, which is shown in the art for canola separation, in combination with the unique processing steps disclosed herein.

In an embodiment, the protein isolate comprises less than 2% (w/w) of oil. In a further embodiment, the protein isolate comprises at least 80%, 85%, 90%, 95% or greater protein (w/w) on a dry weight basis.

In a further embodiment, the oilseed comprises canola (such as *Brassica juncea* or *Brassica napus*), rapeseed, mustard seed, broccoli seed, flax seed, cotton seed, hemp seed, safflower seed, sesame seed or soybean or an oilseed meal produced therefrom, optionally canola meal.

In a further embodiment, the process is a batch, semi-continuous or continuous process or a combination thereof.

In another embodiment, the solid phase is dried and solvent extracted to isolate oil.

Canola Pressed Cake Production

Described herein is a cold crush manufacturing process incorporating features of the invention for production of a low oil content canola oilseed meal, also referred to as a press cake, with essentially non-denatured proteins for subsequent processing to produce a fully soluble protein isolate of >80% (DWB), more preferably >90% (DWB).

Table 1 lists the difference between cold crush process incorporating features of the invention and typical hexane crush and cold pressing operations as described in the prior art. The cake from the current process is then further processed to produce a protein Isolate without the use of organic solvents (such as hexane) to remove the oil remaining in the cake after pressing.

In the cold crush process used herein substantially the same equipment is used as is used in typical prior art hexane crush facilities. However, the residence time (20-30 min vs 45-60 min, total conditioning time) and the temperatures (60-70° C. and 80-85° C. vs 100-105° C. and 105-115° C. respectively) used in the flake conditioning process and pressing process set forth herein are significantly different from the typical hexane crush facility. These processing differences result in a significant reduction or elimination of denaturing while still providing a press cake containing 12-14% oil compared to 15-20% oil for hexane crushing operations, which also result in denatured protein. Prior art cold press facilities use less equipment and steps than either the present cold press process or the hexane crush facilities but do not achieve or control temperature to levels as low as the present low temperature process.

TABLE 1

| | Process Cold Crush | Prior art Hexane Crush | Prior art Cold Pressing | Process Cold Crush | Prior art Hexane Crush | Prior art Cold Pressing |
|---|---|---|---|---|---|---|
| | | | | Temperature (° C.) | | |
| Seed Cleaning | ✓ | ✓ | ✓ | Ambient | | |
| Pre-Conditioning | ✓ | ✓ | | 40-45 | 20-35 | |
| Flaking | ✓ | ✓ | | 40-45 | 20-35 | |
| Conditioning | ✓ | ✓ | ✓ | 60-70 | 100-105 | 95-105 |
| Pressing | ✓ | ✓ | ✓ | 80-85 | 105-115 | 95-105 |
| Cake breaking | ✓ | ✓ | ✓ | ✓ | ✓ | ✓ |
| Cake cooling | ✓ | | Opt. | 25-40 | | |

| | | | | Oil content Cake (%) | | |
|---|---|---|---|---|---|---|
| | Duration (min.) | | | Full Press | Pre-Press | Full-Press |
| Seed Cleaning | | | | | | |
| Pre-Conditioning | | | | | | |
| Flaking | | | | | | |
| Conditioning | 20-30 | 45-60 | 45-60 | | | |
| Pressing | | | | 12-14% | 15-20% | 10-14% |
| Cake breaking | | | | | | |
| Cake cooling | | | | | | |

In more detail, the process steps are as follows:

Seed Receiving and Storage—Canola (*B. Napus, B. Juncea, B. Rapa*) seed has a moisture level of less than 10.5% measured per the Canadian Grain Commission's grain grading guide. The seed can be stored in silos until required for the crush process.

Seed Cleaning—Product is conveyed to a rotary cleaner for removal of foreign material by screening and aspiration with the by-product going to a dedicated storage bin.

Pre-conditioning—The seed is pre-heated, optionally using a vertical conditioner. The seed passes over pipes which are heated with low pressure steam to heat the seed to 40-45° C. before flaking. The pre-conditioning of the seed, particularly in the winter when the exterior temperatures can be below freezing, (educes the seed shattering that can occur during the flaking process. The pre-conditioning produces a more suitable quality flake which in turn improves the performance and oil removal in the press while reducing the amount of fines which that pass through the press with the oil. Excessive fines in the oil increases the cost of oil refining and, because the fines contain soluble protein, also reduces the protein yield in the protein isolate process. The preferred processing equipment is a vertical conditioner of a "First In First Out" (FIFO) design. The Pre-conditioning process is in principal the same as is used in a hexane crush facility. However, in the hexane crush industry the seed are usually heated only to 20-35° C. It has been determined, for production of a superior isolate, pre-conditioning to 40-45° C. produces a lower oil content cake with a higher PDI (Protein Dispersibility Index), which is an indication of a lower protein denaturation than when pre-conditioning only to 20-30° C.

Flaking: To maximize the oil recovery the seed has to be physically broken up before being pressed. Whole seed at a temperature of 40-45° C. is squeezed between two rotating cylinders and flattened to a thickness of about 0.2 to 0.4 mm.

Conditioning—the flaked Canola seed is then warmed to 60-70° C. for ½ hour (65° C. preferred). The conditioning temperatures for the seed in the North American hexane crush industry are typically 100-105° C. with a typical residence time of 45-60 minutes. The moisture level in the flaked seed required for optimum pressing in the hexane crush industry is 2.5 to 3.5%, which is significantly lower than the 6 to 7% moisture content in seed conditioned preferred for the currently described cold crush and press operation. Optimum moisture levels for good pressing may be very dependent and specific to type and manufacturer of press as well as press operating temperature.

Pressing—The conditioned seed is then pressed to separate oil from the press cake. The preferred press, (French Oil Mill Machinery Company, USA) is non-typical of the hexane crush industry in that it has both shaft and cage cooling and an adjustable cone. In contrast, because the hexane crush industry operates at much higher temperatures they do not control the temperatures created in the press and do not use shaft cooling or adjustable cones. French Oil is believed to be the only company that manufactures a press with cage cooling. However, French Oil equipment is typically used in prior art cold pressing operations. In the present described process the shaft cooling is believed to help achieve lower oil content in the cake. Likewise, the cage cooling helps in producing lower oil content cake but its major benefit is that it keeps the cake temperature cool during pressing (nominally less than 5 mins. residence time) and provides an increasing oil viscosity such that fewer fines are lost through the cages of the press into the oil stream. A further benefit is that the oil removal can be increased by increasing the spacing between cages without increasing the fines lost to the oil which would in turn increase subsequent oil refining costs. The adjustable cone allows for more flexibility in optimizing pressing conditions in achieving both low oil content in the cake while providing a superior cake with a higher PDI.

Oil Refining—The oil is then further processed to provide a super-degummed canola oil which can be shipped long distances without settling of gums for subsequent processing into food grade canola oil.

Cake-Breaking—The press cake is broken up to reduce the particle size so that the cake can be more easily conveyed. Performing the breaking process either before or after cooling does not change the quality of the proteins.

Cake cooling—The press cake is cooled to less than 40° C. to lengthen the time the cake can be stored in a hopper before being conveyed to the subsequent protein isolate process described below. Cake cooling is not typical used in the hexane crush industry but is likely used by prior art cold press operations to improve safety of storing cake in silos before shipping. Depending on oil content, not cooling the cake can result in over heating during storing, which in turn can result in reduced cake quality.

As pointed out above, while there are some similarities in equipment and processing steps with prior art hexane or cold pressing operations, there are several differences, particularly in temperature and processing times, and these differences are critical to the oil content and quality of the protein, particular the solubility of the protein in the seed cake produced and the quality of the isolate prepared from this seed cake. During a hexane crush operation, proteins are denatured at a minimum of two steps of the typical prior art process;

The flake conditioning step where flaked seed is heated to 105° C. for an extended period of time, and The desolventizing toaster where the hexane oil extracted meal is heated with live steam to remove residual hexane.

The present process does not use solvent (hexane) to produce isolates and therefore does not at any point have to increase the temperature to recover and remove solvent form the meal and/or proteins. The conditioning process of the process set forth herein is thus substantially different from both typical hexane crush processes and from typical cold pressing operations.

The above described process operates below the denaturing temperature of the proteins of the oilseed. For example, the process operates below the denaturing temperature of cruciferin protein, which results in little or no denaturation. Cruciferin is the canola protein with the lowest thermal degradation temperature.

The temperatures are maintained below 85° C. during the crush process. This study also supports the finding that typical hexane crush and cold press operations will significantly denature the proteins in the seed.

The data provided in the Table 2 below confirms that the above described process causes little or no denaturation of the proteins contained in Brassica Juncea or Brassica napus seeds being processed according to the above described procedure.

TABLE 2

| Sample ID | Seed Source | Moisture & Volatiles (%) | Protein (%) Leco | PDI Leco (AOCS) | PDI Leco (AOCS) Non-defatted |
|---|---|---|---|---|---|
| 2011-10-12 Seed | B. juncea | 7.1 | 42 | 33 | 19 |
| 2011-10-13 Pre-Cond Flake | B. juncea | 8.0 | 42 | 33 | 26 |
| 2011-10-11 Conditioned Flake | B. juncea | 7.7 | 42 | 32 | 27 |
| 2011-10-11 Press Cake | B. juncea | 7.6 | 41 | 35 | 24 |
| 2012-01-06 Seed | B. napus | 6.5* | 42 | 51 | 28** |
| 2012-01-08, 09, 10 Press Cake (average value) | B. napus | 8.1* | 42 | 45 | 35 |

*reported on an as-is basis (non-defatted);
**average of two loads of seed

Statistically there is no difference in the above analysis of Protein Content and Protein Dispersibility Index (AOCS) from seed to pressed cake in the above described process facility, the resultant press cake having an oil content of 12-14%. The above characterized press cake was then further processed into protein isolate as described below.

In order to determine PDI, all of the samples were extracted with hexane and dried at lower temperature to ensure the oil content was lower than 3% and that there was no denaturing of proteins. The PDI analysis is affected by oil content and reduces the measured PDI on samples with higher oil content. While the results in the last column in Table 2 show variability in the PDI analysis on non-defatted seed, flake and press cake samples, the variability in these samples is higher than in defatted samples. The above analyses were all for samples collected at the same time at the designated four different points in the crush process.

Aqueous Processing of Pressed Cake

It was found that when meal with about 14% oil is added to water, the oil principally stays in the meal. However, protein extraction by water is largely unaffected by the presence of oil in the meal and a fraction of the oil is released from the partially defatted meal by the addition of the water used for extracting the soluble protein. That oil then floats on the surface of the water after a separation process.

Figure 4:
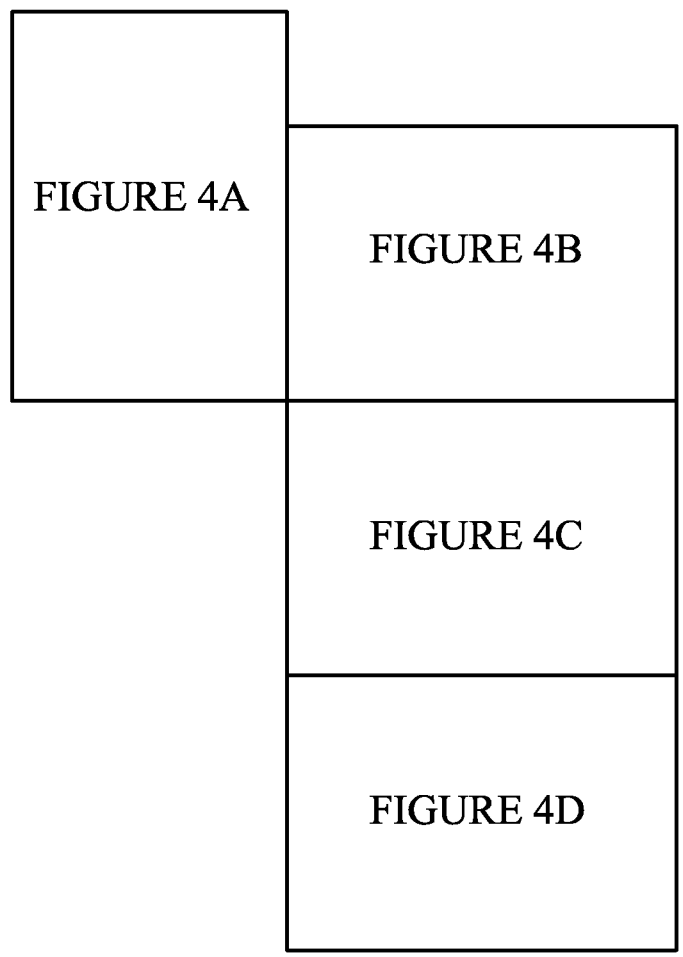
FIGS. 4A, 4B, 4C and 4D represent a single process flow diagram, which is a schematic diagram showing the various steps in separating canola press cake into the insoluble and soluble portions; the Figure comprises four pages with the first page, designated FIG. 4, being a box diagram showing the relationship of the subsequent four pages labeled FIGS. 4A, 4B, 4C and 4D.
Figure 4A:
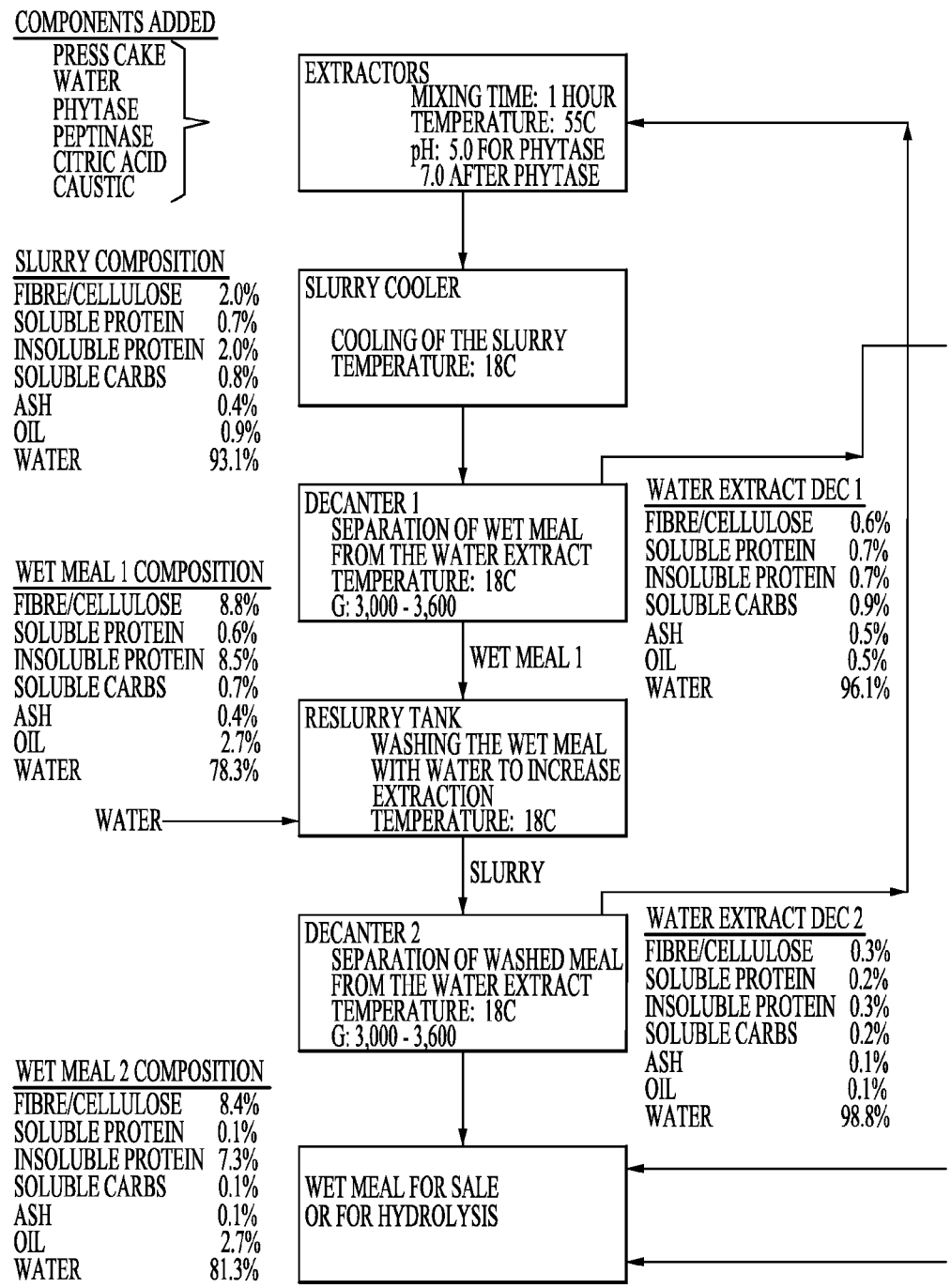
Figure 4B:
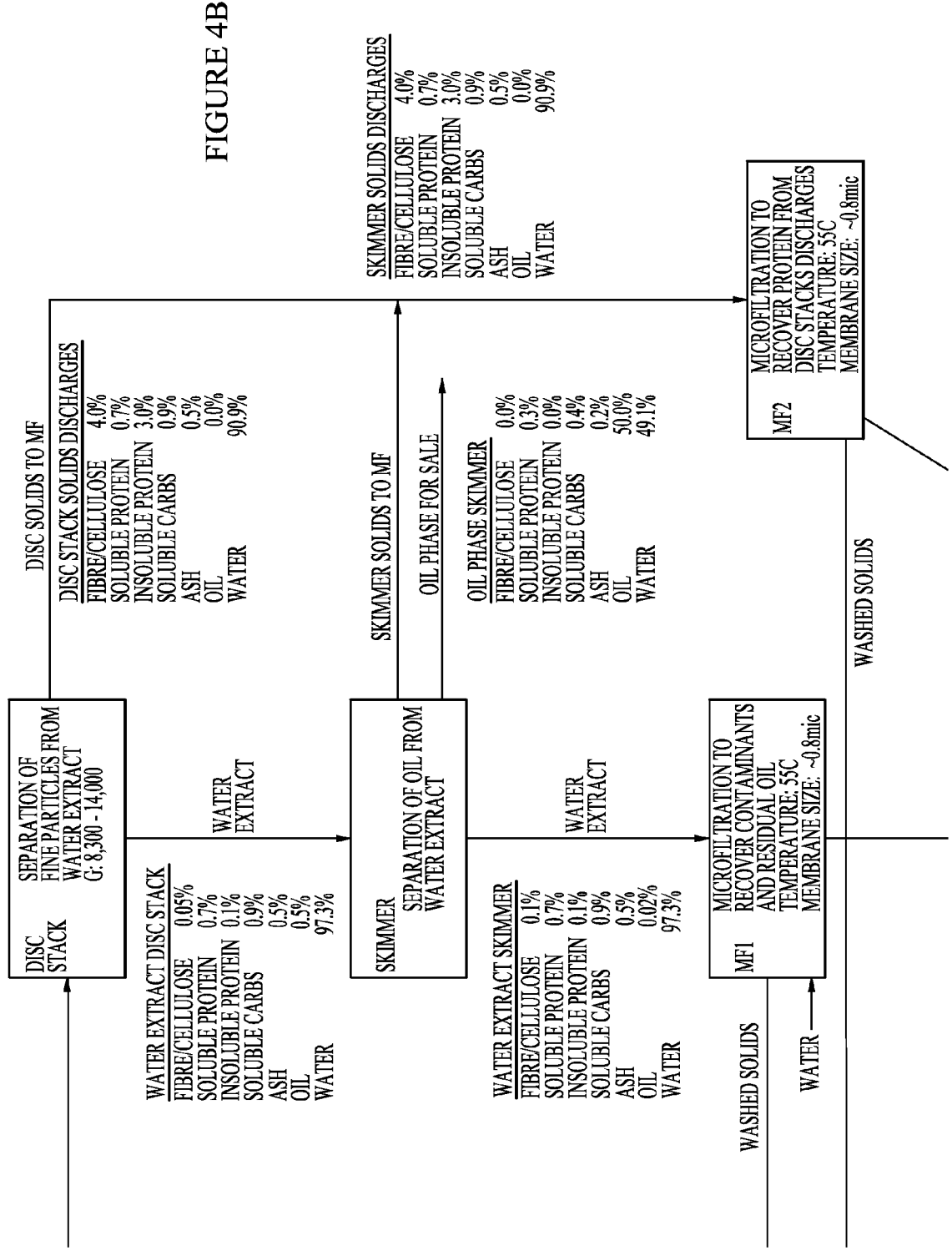
Figure 4C:
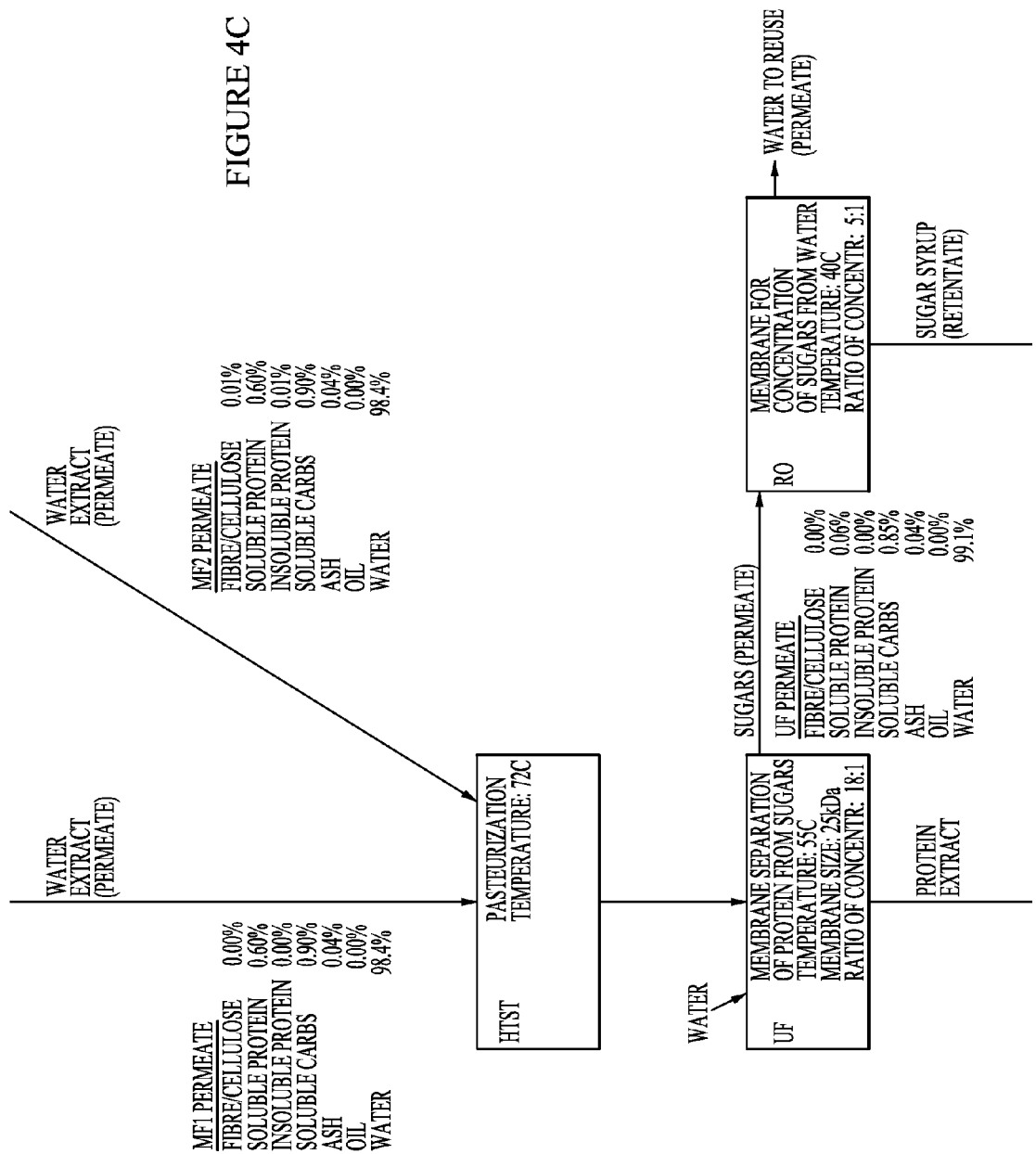
Figure 4D:
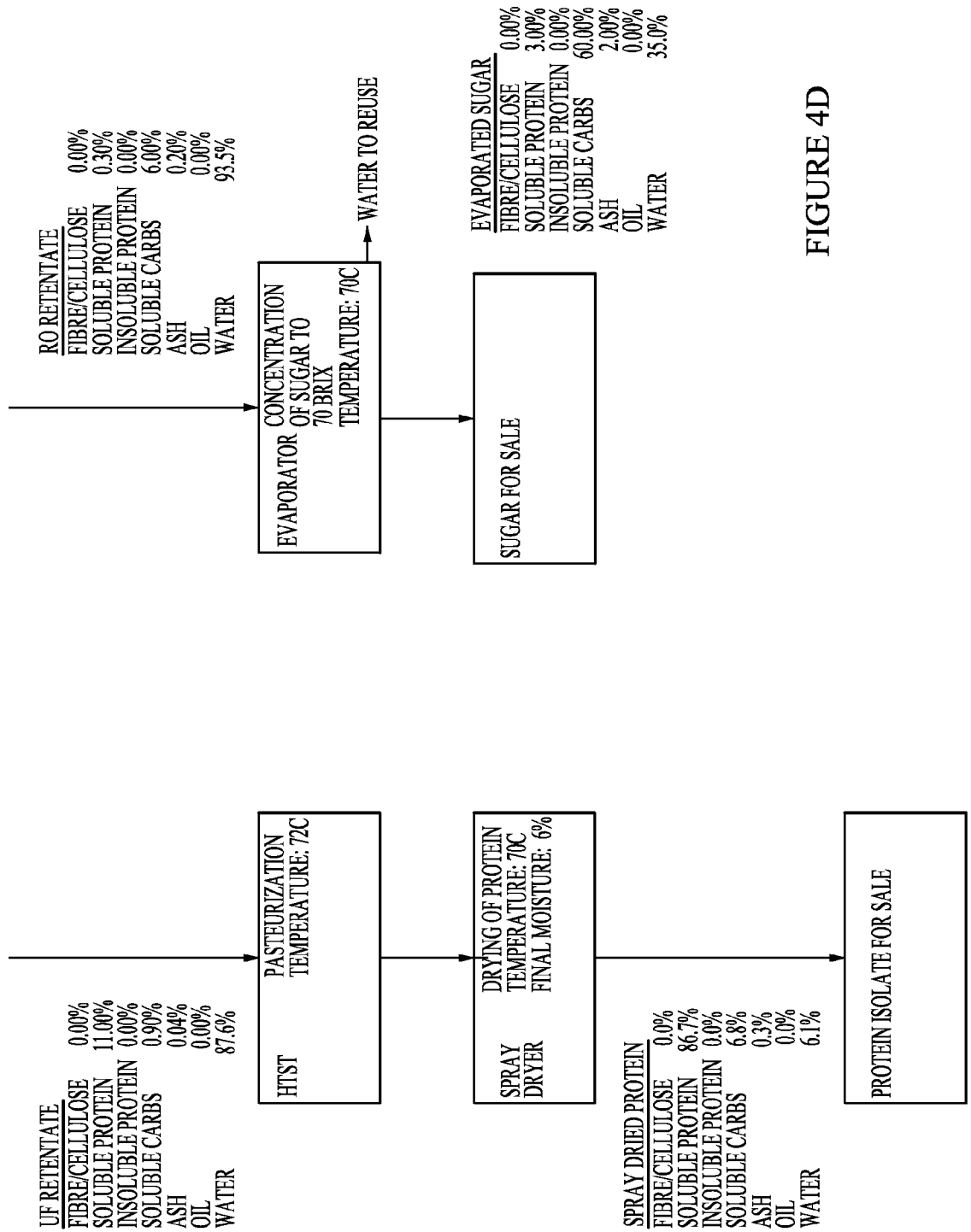

A skimming centrifuge, or two skimming centrifuges in series, can be used to extract the oil from the liquid phase as a result of centrifugal forces applied. Meal, water, and phytase were mixed for about 1 hour. The slurry was separated into a solids and a liquid phase and the liquid phase was delivered to a skimming centrifuge followed by processing using elevated temperature (70° C.) short term pasteurization (HTST), ultra filtration (UF) and spray drying (SD). Extraction is conducted using only water as the solvent. The flow charts shown in FIGS. 4A-B schematically shows the process. As shown in FIG. 4A-B, microfiltration can be added between the oil skimming and HTST steps to decrease the oil and insoluble content of the spray dried isolate.

This procedure provides the ability to rapidly process and produce a significant quantity of protein and minimizing fines, emulsions, and eliminating the requirement to recover organic solvent and avoid flashing. An appropriate centrifuge such as used in the milk or citrus industry, preferably one or two in series, is used to skim the oil from the aqueous phase. It should be noted as well that the skimmer can be located at any stage of the process, including after the decanter and before the UF system.

EXAMPLE 1

14% meal from the crushing process was added to water (7:1 water:meal (m/m)) and the solids decanted from the liquids. The liquid phase had a yellow, semi-solid floating phase on top of the water phase. Upon drying the entire water phase, including the floating yellow phase, 100 mL of solution provided about 5% dissolved solids containing 40-47% protein which is consistent with hexane extracted meal. The oil content of the water phase on a dry weight basis (dwb) was from 1.4%-9.4%. However, if the yellow oil phase floating on the surface is removed before drying, the oil content of the dry, dissolved solids was reduced to 0.5-0.7%. The amount of oil present in the sample is approximately 30-50 mg in 5 grams of sample. It was found that the yellow floating oil phase could be readily removed via skimming or other oil removal techniques and then the remaining supernatant could be processed through the UF to produce a protein isolate with <2% oil.

EXAMPLE 2

In a second evaluation 225 g of cold-pressed meal (containing 14% oil) was added to 50° C. water (8:1 water:meal (m/m) to form a slurry. The slurry was mixed, 0.6% phytase was added, and the slurry stirred for one hour. At the end of one hour, the pH was adjusted to 7 and then decanted to remove the solids. The liquid phase was further centrifuged and the oil phase was removed from the surface of the solution. The above procedure was repeated 4 times, generating 3.9 L of feed.

The decanted and skimmed water phase, was ultrafiltered using a UF system (Millipore, 10 kDa cutoff membrane). The water phase was reduced in volume to 500 mL (ca. 8× concentration) and then diafiltered 4× with 2800 mL of water (700 mL per diavolume). The UF retentate/feed was maintained at 40° C. during concentration and diafiltration. After emptying the UF lines and membrane housing, a total of 700 mL of retentate was obtained.

The retentate was cooled overnight to 2-8° C. and then spray dried (Buchi, lab-scale spray dryer). Typical spray drying conditions were a 180° C. inlet temperature and >70° C. outlet temperature. A total of 23.8 grams of powder was obtained. (A considerable quantity of end product was lost in the spray dryer because of the small amount of feed to the spray dryer and losses due to material retained in the lab-scale, general use spray dryer). The proximate analysis of this powder is shown in Table 3.

TABLE 3

Proximate Analysis

| Protein (dwb) | 98% (91% as is) |
|---|---|
| Ash | ND |
| Oil | 1.6% |
| Fibre | ND |
| Moisture | 6.7% |

The protein powder was light tan in color with minimal aroma and had a slight bitter taste that didn't linger.

The skimming technique that led up to this end result was repeated several times with the results shown in Table 4

TABLE 4

| | Before Skimming (mg oil/g solids) [% oil] | After Skimming (mg oil/g solids) [% oil] |
|---|---|---|
| 1 | 55 [5.8%] | 6 [0.7%] |
| 2 | 55 [5.8%] | 6 [0.7%] |
| 3 | 91 [9.1%] | 5 [0.6%] |
| 4 | 94 [9.4%] | 6 [0.6%] |

It was found that the floating oil phase can be effectively and continuously removed via a continuous process, such as a dairy or citrus juice centrifuge or similar device. The process has several advantages: 1) short total residence time in the plant (pre-spray dryer) 2) no solvent and 3) allows continuous production of high quality soluble protein.

As shown in Table 5 below, *Brassica Juncea* and *Brassica Napus* seeds provide comparable protein isolate products when processed using the processes of the present disclosure.

TABLE 5

| Analysis Protein Spec | Units | SPEC | Juncea | Napus |
|---|---|---|---|---|
| Protein (Dwb) | % | ≥90 | 90.6 | 90.9 |
| Protein (As is) | % | ≥85 | 85.9 | 86.1 |
| Soluble Crude Protein (As is) | % | | 85.7 | 86 |
| Soluble Crude Protein (CP) INDEX | % | | 99.81 | 99.86 |
| Moisture & Volatile | % | <7 | 5.15 | 5.25 |
| Fat (Oil Content) Swedish tube | % | | 2.06 | 1.56 |
| Ash | % | <4 | 3.8 | 1.6 |
| Aerobic plate Count (SPC) | cfu/g | <10,000 | 140 | 2200 |
| E. Coli | cfu/g | −'ve/10 g | −ve | −ve |
| Salmonella | cfu/g | −'ve/25 g | −ve | −ve |
| Yeast & Mold | cfu/g | <100 | 10 | 10 |
| Yeast | cfu/g | | −ve | −ve |
| Mold | cfu/g | | −ve | −ve |
| Powder appearance | | tan | | |
| Colourimetric (dry) | Hunter | >L 70 | 66.95 | 63.83 |
| Colourimetric (Liq 1% @pH 7) | Hunter | >L 40 | 60.60 | 55.59 |
| Bulk (tap) Density | g/ml | >0.25 | 0.262 | 0.289 |
| Pass through US 80 Mesh | % | >90 | 95 | 95 |
| Bulk Density | g/ml | >.25 | 0.176 | 0.193 |

Use of Processing Enzymes to Remove Insolubles

In a preferred process, enzymes are used to destroy soluble fiber and other entities not protein related (cellulose, hemicellulose, pectin, etc.) so they can be readily removed. These constituents can result in an end product with protein levels >90%. Enzymes are used to breakup these undesirable materials so that they can pass through the UF membrane (10,000

Da). Two enzymes, Crystalzyme® and Validase® were evaluated for this purpose. One skilled in the art based on the teachings herein will recognize that other similarly acting enzymes can also be used. Crystalzyme® and Validase® are registered trademarks of DSM IP Assets B. V. Corporation, Heerlen, Netherlands.

Validase TRL is a multi-component enzyme system produced by the controlled fermentation of a nongenetically modified strain of *Trichoderma longibrachiatum* (aka *T. reesei*). The enzyme system includes a multi-cellulase complex and hemicellulases that hydrolyze and depolymerize (break down) structural and non-structural carbohydrates (polysaccharides) in plant derived foods and feedstuffs (galactosidase, glucanases, manannase, and xylanase).

Crystalzyme PMLX is a proprietary enzyme system produced by the controlled fermentations of nongenetically modified strains of *Aspergillus niger* and *Trichoderma reesei*. The enzyme system includes pectinases, cellulases, hemicellulases, and arabinase. Crystalzyme PMLX hydrolyzes and depolymerizes (breaks down) fruit and vegetable pectin and other selected complex polysaccharides.

Food-grade Crystalzyme and Validase enzymes were added to the slurry at the same stage in the process as the phytase addition. Both enzymes (Validase and Crystalzyme) have maximal activity at pH 5 and a temperature of 53±2° C., which is consistent with the operating conditions for use of Phytase. As an initial evaluation, based on suggested dosing in the product literature, an initial dose of 800 mL of Crystalzyme was added to a single extractor load of slurry. While an analysis of the in-process data did not show an improvement in decanter performance with this enzyme at this dosage level, there was a slight improvement in protein purity. As an alternative, also based on product literature dosing recommendations, 100 mL of Validase was added to the same size extractor load of slurry. In contrast to Crystalzyme, Validase provided an improvement in decanter performance, as evidenced by the in-process data, and the protein purity was increased by about 2% (to 86% (dwb)) over base line values.

It was also found that temperatures in the decanting process affected the purity of the end product with higher temperatures >40° C., as opposed to operating the decanter at <20° C., reducing the protein purity to below 80%. FIG. 1 shows the relationship of the decanter operating temperature on final product purity when the properties of the slurry feed to the decanter and the downstream processing conditions are held constant. On this basis, when the temperature of primary decanting was reduced to <20° C. protein purity levels in the final end product were >86%.

The presence of insoluble components from a process stream will have an effect on the purity of the final product produced where only the soluble components are desired. It is also known that decanting (or centrifugation in general) is affected by the temperature at which the decantation process is carried out because the temperature affects the viscosity of the solution, which in turn affects the centrifugation performance (Stokes Law). As temperature is decreased the viscosity increases and as such the ability of insoluble particles to move through the solution under the influence of G force is reduced by the higher viscosity at the lower temperature. This in turn affects the ability of a continuous centrifuge to remove the insoluble particles, thus adversely affecting purity. On the other hand increasing temperature lowers viscosity, therefore improving clearance of insoluble particles. For this reason, centrifuge manufacturers typically recommend running a process at the highest temperature possible in order to maximize separation performance.

By following centrifuge manufacture recommendation and increasing primary decanting temperature to take advantage of improved insoluble solids removal, clearance of insoluble solids improved. However, purity of the final product was reduced because the elevated temperature caused more of the undesirable insoluble solids to become dissolved and carried into the final product, thus reducing the protein concentration in that final product. This result was unexpected.

It was discovered that as the temperature during primary decanting decreased, purity of the final product improved and the trend is linear. A best balance of the decanting operation with purity appears when primary decanting is conducted at 18° C. When the decanting operation is performed at above 25° C., the purity of the product is reduced to below 80%, as shown in FIG. 1. The two points at the lower temperatures (decanter temperature of <20° C.) with a purity of less than 80% were the result of processing a feed stream sample with a higher concentration of impurities and problems with oil removal in downstream equipment and are not indicative of the relationship between decanter operating temperature and end product purity.

Phytase Delivery

Phytates found in plant materials are an anti-nutritional factor that can be destroyed by using the enzyme Phytase. The evaluation described below sets forth studies conducted to compare use of BASF Phytase with DSM food-grade, Kosher phytase and determine dosing levels, temperatures, processing times and other process variables for the use of DSM phytase for the reduction or elimination of phytate in the end products. The comparison, initially performed on freeze-dried slurry, is shown in Tables 6-12.

Samples were generated by heating water to 52±2° C., adding partially de-fatted meal to the water, and then adding a pre-determined amount of phytase to the slurry. 15 minutes of vigorous mixing was used to create a slurry before adding in phytase. At each dosing residence times of 30, 60, 90, and 120 minutes were evaluated. For reference, a control sample was prepared according to the above (holding for 1 hour), but without the addition of Phytase. The control sample had a phytate level of 2.9%.

TABLE 6

Phytate Levels, %

| | DSM | BASF* | DSM | BASF* | DSM | BASF* |
|---|---|---|---|---|---|---|
| Phytase dose, % | 0.3 | | 0.6 | | 1.0 | |
| 30 minutes | 2.5 | 2.8 | 1.6 | 2.3 | 1.4 | 2.4 |
| 60 minutes | 2.4 | 2.5 | 1.6 | 2.3 | 1.5 | 2.1 |
| 90 minutes | 2.0 | 2.3 | 1.5 | 2.1 | 1.5 | 2.1 |
| 120 minutes | 1.7 | 2.5 | 1.3 | 1.9 | 1.3 | 1.9 |

*BASF Phytase dosing was actually 0.2%, not 0.3%, due to the differences in concentration: BASF 10,000 FTU/g vs. DSM 5,000 FTU/mL. The concentration of BASF material is twice that of DSM so that the amount of DSM material dosed must be doubled in order to deliver the same amount of FTU's to the reaction. According to DSM, 50 mg of enzyme has 100 FTU's. Thus, the same amount of enzyme was effectively added. In all other cases where a direct comparison has been made (Tables 6-8), the effective amount of enzyme added is the same.

Table 7 sets forth the values from Table 6 comparing DSM and BASF Phytase at each dosing level after an hour of reaction.

TABLE 7

Phytate levels Comparison at 1 hour

|      | 0.3% | 0.6% | 1%  |
|------|------|------|-----|
| DSM  | 2.4  | 1.6  | 1.5 |
| BASF | 2.5  | 2.3  | 2.1 |

In terms of performance, there is marginal difference between DSM Phytase dosing of 0.3% but there is a difference between 0.6% and 1%, indicating that a suitable dosage is between 0.6 and 1% for the greatest reduction of phytate. The slurry still contained recalcitrant phytate that was not attacked and destroyed by the enzyme when delivered as described above. One skilled in the art will recognize that DSN and BASF are examples of suitable phytase. Other sources of phytase are also available.

To further address the recalcitrant phytate, treated samples were centrifuged and analyzed. Following centrifugation of the solids it was found that the phytate levels are dramatically reduced. Table 8 shows the phytate level in the liquid extract compared to the slurry phytate level using DSM phytase was about one-half of

TABLE 8

Liquid vs. Slurry
Dosing for 1 hour

| Dose | Slurry | Liquid extract |
|------|--------|----------------|
| 0.3% | 2.4    | 1.2            |
| 0.6% | 1.6    | 0.7            |
| 1%   | 1.5    | 0.6            |

Water-meal contact time prior to phytate addition was also found to have an impact on the phytate levels in the final product. The meal is preferably fully hydrated in order for the phytate in the meal to come into contact with Phytase for effective reactions to occur. If contact is prevented because water had not accessed all of the meal interstices, then a significant reduction in reaction will result and phytate levels will remain high. Thus a high level of hydration is preferred for phytate destruction. To evaluate the effect of water-meal contact time, meal was mixed with water for various time periods before DSM Phytase was added. All samples were treated in the same manner with the only variable being the amount of mixing time prior to Phytase addition.

Table 9 shows the phytate levels following ultrafiltration for several different hydration times prior to phytase addition. Phytate levels drop as a result of extended hydration from increased incubation time prior to phytase addition.

Another aspect is that the BASF Phytase, a granulated powder, must be fully dissolved and dispersed in order for a proper reaction to occur. The rate of reaction can be affected by inconsistent dissolution rate due to mixing dynamics; better mixing dynamics (i.e. pumping, shear, tank turnovers, etc.) results in faster Phytase dispersion and a greater extent of reaction. Providing Phytase as a liquid (DSM Phytase) does not suffer from the dispersion issues encountered with solid Phytase.

TABLE 9

Phytates Levels following UF Processing

| Time of mixing prior to Phytase addition | Phytate % |
|------------------------------------------|-----------|
| 15 minutes                               | 0.53      |
| 2 hours                                  | 0.49      |
| 4 hours                                  | 0.37      |

Based on the above data, there is recalcitrant phytate in the slurry after treatment. After centrifugation, the level of phytates in the liquid stream is about half that of the slurry and the amount of phytate drops by about half following concentration in the UF.

Additional evaluation of adjustments made to other steps in the full-scale process were evaluated for efficacy in resolving phytate results >1% in the end product.

EXAMPLE 3

For these evaluations, water to meal slurry of 10:1 ratio was used. The meal slurry was stirred on hot plate for approx. 1 hour at ≤52° C. to completely breakdown the meal. Table 10 shows the steps of heating, Phytase additions, hold time, pH adjustments, etc. Different quantities of Phytase were used to account for the different concentrations from each supplier. The first and second columns compare the same concentration of phytase from the two sources. The third column provides data for DSM using a different method of addition, i.e. the Phytase was added to the RO water or to the slurry and at a slightly higher temperature (≤58° C.). After digestion, the slurries were centrifuged to separate the meal fraction from the supernatant. 250 ml samples were centrifuged at 4000 rpm (2700 G) for 10 minutes using a Thermo Scientific, Model CL31 centrifuge. The supernatant was then analyzed for Phytate (Phytic acid) on an 'as is' liquid basis.

TABLE 10

Procedure steps

| Steps | BASF (10,000 G) Granular | DSM (5,000 L) Liquid | DSM (5,000 L) Liquid (w RO water) |
|-------|--------------------------|----------------------|-----------------------------------|
| Water (g) | 401.06 | 402.87 | 400.60 |
| Temp (° C.) | — | — | 58 |
| Phytase Addition (g) | — | — | 0.210 g |
| Hold Time (hr) | — | — | 1 hr |
| Meal (g) | 40.07 | 40.31 | 40.27 g |
| Temp (° C.) | 52 | 52 | 58 |
| pH (Start) | 5.79 | 5.76 | 5.74 |
| pH 5.0 (adjusted with 10% Citric Acid) | 8 ml | 8 ml | 5 ml |
| Phytase Addition (g) | 0.1244 | 0.2422 g | — |
| Hold time (hr) | 1 hr | 1 hr | 1 hr |
| pH (End) | 5.41 | 5.39 | 5.23 |
| pH 7.0 (with 0.2N NaOH) | 78 ml | 78 ml | 80 ml |
| Centrifuge/decant | yes | yes | yes |

Results:

| | Sample ID (Supernatant liquid) | | |
|---|---|---|---|
| | JF-02-143-BASF | JF-02-143-DSM | JF-02-143-DSM-RO |
| Phytate (Phytic Acid) As is | 0.37% | 0.35% | 0.39% |

In one embodiment, the process utilizes DSM phytase.

The following changes over the prior procedure were implemented:

1) Order of addition—the enzyme was added in after the meal was added to the RO Water because the meal adds ions to the water. Previously, the enzyme was added to RO water at temperature before the meal was added. However, RO water is non-ionic which can cause stress to the enzyme and potentially denature the enzyme rendering it inert.

2) RO water temperature—the temperature of the water added to the extractors was reduced to 53±2° C. The optimal enzyme temperature is 55° C. with the understanding that it is better to be below 55° C. than above. In prior procedures the temperature tended to be 56-60° C. which was above the optimum for enzymatic activity.

3) A step was added to the process to reduce the slurry's pH to 5±0.2 before enzyme introduction. This change places the enzyme in an environment where the enzyme is most active.

4) Because the amount of phytate in meal may vary the phytate levels in the feed are monitored and the amount of enzyme adjusted to maintain the level of phytate in the end product below 1%.

Filtration for Phytate Removal

A key unit operation in the process with respect to product purity is the UF/DF system. These operations provide the means to clear unbound phytates (i.e. not bound to protein) from the retentate, resulting in a purer product. To evaluate the effect of the UF/DF system, water was heated to 52±2° C. and partially de-fatted meal was added. The meal was mixed until suitably dispersed/suspended. 0.6% Phytase (v/w) was added and held for 1 hr at the indicated temperature and solids were removed via centrifugation. The meal was washed with 2.5× the mass of the heavies and the liquid extracts combined. The sample was concentrated using an ultrafiltration device fitted with 10,000 MWCO membranes and then diafiltered. Samples were removed prior to concentration, after concentration, and then after each diavolume was processed and tested for phytate residue. The data is shown in Table 11.

TABLE 11

Phytates as a Result of UF Processing

| | Phytate % |
|---|---|
| Liquid Extract (after centrifugation) | 0.5-0.7 |
| Concentrated Extract | 0.25 |
| Diavolume 1 (retentate tested) | 0.23 |
| Diavolume 5 (retentate tested) | 0.22 |

Table 12 shows phytate results in the final product before and after the above changes were fully implemented, with batch 20110725 incorporating all of the above changes.

TABLE 12

Phytate Results From Production Samples

| | Batch # | | | | |
|---|---|---|---|---|---|
| | 20110718 | 20110719 | 20110720 | 20110725 | 20110726 |
| Phytate, % | 1.90 | 2.30 | 0.72 | 0.42 | 0.56 |

Evaluation of Three-Phase Centrifuge (Oil Skimming)

Previously, it had been shown that the bulk of the fat present in the water phase (ca. 2-10% oil on a dwb of the solids in the liquid phase) could be manually separated. A three phase, continuous centrifuge was evaluated for the continuous removal of oil (and the yellow phase) which had separated from an aqueous processing stream generated by mixing meal and water following solids removal therefrom, either with or without prior defatting of the meal and the product exiting the centrifuge was suitable for the production of a protein isolate following subsequent ultrafiltration, diafiltration, and spray drying. In general, we have shown that oil contents upwards of 10% oil (dwb) of the dissolved solids can be effectively defatted by manual skimming following a brief exposure to G force (ca. 2900 G).

The starting material was canola seed that had been cold pressed to achieve oil levels of 14 and 18%, respectively, in the meal. Temperature control was used to retain the native solubility of the protein (PDI=30). Canola meal (600 kg) was added to water (4200 L) at 50±5° C. under good agitation. Food-grade phytase was added (0.6% v/w (meal)) and the slurry was mixed for 1 hour. The pH was then adjusted to 7 and the solids removed from the liquid phase using a continuous decanter centrifuge. The liquid phase was then treated by HTST (72-74° C.) followed by residual insoluble solids removal using a solid/liquid (2 phase) clarifier.

The liquid, containing soluble protein and residual oil, was then processing through a continuous oil skimming centrifuge operating in a 3 phase mode (solids/liquid/liquid). This provided further removal of residual solids as well as removal of residual oil from the water phase. The water phase contained protein and sugar (ca. 40-48% of the solids present in the water are protein and the balance sugar, ash, and other soluble components).

EXAMPLE 4

Two different starting materials were employed: 1) 14±1% oil-containing press cake, and 2) 18±1% oil-containing press cake. The purpose of this was to verify that the load of incoming oil did not adversely affect the process. Two different temperatures were also evaluated 1) 15±1° C. and 2) 40±1° C. to determine whether or not temperature plays a role in the ability to remove oil and the efficacy of oil removal. Prior lab studies showed that batch separation of the oil layer by centrifugation and skimming was facilitated by colder temperature (see Table 13). However, because continuous centrifuges often work better at warmer temperature this was once again evaluated.

TABLE 13

Temperature Effect on Batch Oil Removal

| Sample | Temperature | Oil Recovered (mg/100 mL process solution) | % oil (dwb) of solids |
|---|---|---|---|
| Control | no skimming | 153 | 3% |
| 1 | 15° C. | 6 | 0.1% |
| 2 | 40° C. | 17 | 0.4% |
| 3 | 60° C. | 14 | 0.4% |

Also investigated was the number of passes through the centrifuge required to bring the oil level to an acceptable level. Multiple passes through the centrifuge is indicative of the number of centrifuges needed to be run in series to support the commercial processes in a continuous, one-pass manner. In addition, speed of processing was investigated. The faster a material is fed to the centrifuge, the less the residence time of the material that passes through. Aliquot 1 comprised the water phase from the aqueous extraction of the press cake with 14% oil; aliquot 2 was the water phase from the aqueous extraction of the press cake having 18% oil.

In a first run, 400 L of aliquot 1 was temperature equilibrated to 15±1° C. in an stirred tank. The contents were then fed into the centrifuge at a rate of 120 L/hr. During the course of operation, the bowl was cleared every 45-60 minutes. This was necessary because the solids level was noted to be an issue and the centrifuge internals did not allow for the oil phase to be continuously removed. This allowed the solids to be removed and accumulated oil to be removed. Some of the upper portion of the liquid phase adjacent the oil-level which was removed with the oil was segregated and returned to the tank for further processing. The heavies (containing insoluble solids and some oil collected in the bowl) were collected and weighed separately. The entire first pass through the centrifuge was collected and passed through the centrifuge a second time for 60 minutes.

In a second run, the conditions were the same with the exception that the amount of process solution was reduced to 200 L and the temperature was increased to 40±1° C. The bowl was cleared every 45-60 minutes and then the process was repeated for an additional 60 minutes. The feed rate was 120 L/hr.

The third and fourth runs both used 200 L of feed initially from aliquot 2 processed at 40° C. and 15° C., respectively. The bowl was cleared after 30 min in the run followed by 1 hour for the second pass.

Samples were collected of the feeds (aliquots 1 and 2) and during processing to evaluate the effect of oil removal. The results are tabulated below (Table 14).

TABLE 14

Effect of Oil Removal Using a Skimming Centrifuge

| Sample | Temperature | Oil Recovered (mg/100 mL solution)$^d$ (pass 1) | % oil (dwb) in the solids (pass 1) |
|---|---|---|---|
| Aliquot 1 (Control)$^a$ | No Skimming$^c$ | 394 | 9.2 |
| Aliquot 1 | 15° C. | 6 (26) | 0.2 (0.6) |
| Aliquot 1 | 40° C. | 1 | 0.03 |
| Aliquot 2 (Control)$^b$ | No Skimming$^c$ | 144 | 3.3 |
| Aliquot 2 - 15° C. | 15° C. | (5) | (0.2) |
| Aliquot 2 - 40° C. | 40° C. | 4 | 0.1 |

$^a$derived from 14% cold-pressed press cake (14% denotes residual oil in the press cake).
$^b$derived from 18% cold-pressed press cake (18% denotes residual oil in the press cake).
$^c$Material before conducting oil skimming.
$^d$pass 2 data shown unless indicated in parenthesis.
In the case of aliquots 1 and 2, the sampling of pass 1 for the 40° C. condition was missed. The pass 2 data for aliquot 2, 15° C. was also not taken.

The data clearly shows that the oil skimming centrifuge removes oil effectively from the process stream. By way of comparison, the oil skimming centrifuge removed oil to a level of 1 and 6 mg of oil/100 mL of process solution for 0.03-0.2% oil (dwb) of the dissolved protein.

Filtration Studies

While physical skimming using a multistage centrifuge was found to be an effective means of significant oil reduction, filtration was utilized to further remove undissolved solids and the remaining oil from the dissolved protein in the aqueous extraction solution. Subsequent filtration using a Millipore filter was found to be effective in removing trace oil while maintaining protein purity. A series of Millipore filter sizes (0.22, 0.45, 0.65 um) were evaluated for flux, protein permeability and oil retention. In all trials the recovered volume of feed input ranged from 83 to 93% of the feed.

EXAMPLE 5

0.22 um M.F (Post HTST-Treated Feed)

6.4 L of material was concentrated 12.8 fold and fed through a 0.22 um filter. The 0.22 um filter retained 100% of the available 4 g of oil in the retentate fraction, leaving permeate with <0.01% oil (dwb). Although 57% of the available protein was transferred to the permeate fraction, the significant decrease in flux (80% decrease in flux) was unacceptable. However, it is believed the loss of flux may be a result of proteins size/structure changing due to high temperature exposure while passing through HTST pasteurization unit.

Permeate obtained from this filtration step was then further processed through a lab size UF system to remove sugars and other impurities and the resulting UF retentate was analyzed. A 6 fold concentration of UF feed (Permeate from M.F) was obtained. The UF retentate was then diafiltered with 4 diavolumes to remove the last traces of sugars The output from diafiltration was then spray dried; the protein content was found to be 87.9% (dwb). This showed a significant improvement over material without MF (same mother lot of process solution) which had a purity of only 76.5% (dwb).

Based on this data obtained using the 0.22 um filter, other sizes of Millipore filters were evaluated to optimize the combination of flux, protein recovery and oil retention abilities.
0.45 um M.F (Pre-HTST Feed):

50% of the insoluble matter was first separated from feed using a lab centrifuge. The feed material was then concentrated 12 fold. Based on the test data, the 0.45 um filter retained virtually all of the available 42 g of oil from the feed material either in the retentate fraction or on the filter itself, leaving 0.21% oil (dwb) in the permeate stream.

The feed material was first processed through a Westfalia skimmer and then refrigerated overnight. The feed was concentrated 12.8 fold. Although the filter retained substantially all of the available 3.4 g of oil from the feed, resulting in 0.20% (dwb) in permeate, only 15% of the available protein was transferred to the permeate stream due to the effect of pasteurization on the proteins size/structure.
0.65 um M.F (Post HTST Feed):

The feed material was first processed through a Westfalia skimmer and then refrigerated overnight. The flux rate dropped by 92% during filtering the first 3.5 L of material. The system was shut down after processing 4 L of material since flow had completely stopped. Irrespective thereof, the permeate stream contained only 0.4 g of the available 2.4 g of oil in the feed and 47% of the available protein (dwb) Again this low percentage of protein was attributed to the sample being post HTST and possibly the overnight refrigeration prior to filtering.
0.65 um M.F (Pre Skimmer/Pre HTST):
Test 1—

The flux rate was reduced by 55% (from 200 ml/min to 90 mL/min) during filtering of 6 L of material. However, more than 95% of the available protein was transferred through the filter to the permeate fraction. Based on volumetric mass balance, the feed material was concentrated 20 fold. The volume lost within the system was 500 mL (or 8%). However, 4.3 g of oil from the available 34 g in the feed was transferred to the permeate stream. While this is a high amount of oil transferred compared to the other trials, the feed also had much higher oil content than feed materials in the other filter tests.

Test 2—

A second sample tested with the 0.65 um filter showed an 80% reduction in flux over 6 L, and resulted in a concentration of the feed material by 14.6 times. In regard to flux loss it is important to note that this feed material had the highest level of oil, measuring at 28% (dwb), which may have contributed to flux reduction. The retentate contained approximately 6% (dwb) of the available protein from the feed material, indicating that filtration was successful in transferring the bulk of the protein from the feed to the permeate.

Test 3—

Refrigerated process solution was centrifuged and the oily matter at the surface was skimmed to reduce the overall amount of oil being passed through the Millipore filter. This reduced the oil from 19% to 5% (dwb). The flux rate dropped by 70% from starting flux rate during filtering 5.9 L of feed. The oil transferred to permeate was 0.4 g of the available 9.2 g in the feed material (0.33% dwb), and the protein recovery to permeate was 72% dwb. This high recovery of protein can also, in part, be attributed to the higher reduction on feed volume by 14.8 fold, which transfers more protein to the permeate stream. The refrigeration prior to filtering may have caused the reduced system efficiency.

Test 4—

This material was also skimmed prior to filtering through the MF. The skimmed feed contained 9.22% (dwb) oil or 25.4 g/7.6 L. The flux was reduced by 69% from the starting rate of 61 ml/min during the filtration of 7.6 L. The feed was concentrated 12.6 fold. 1.0 g of oil was transferred to permeate from the 25.4 g available in the feed (or 0.53% dwb). Also, 70.0% of the available soluble feed protein was successfully transferred to the permeate stream during filtration.

In this evaluation, recovery of 70% is lower than the 95% recovery in prior evaluations. Notable differences were:

Feed volume: 20% more volume passing through MF filter per unit area.

Solids/Protein: More solids (12% (dwb)) and 31% (dwb) more protein than test 1.

Oil: Significantly more oil at 35 g than test 2 feed at only 25 g oil, the retentate fraction recovered from test 1 was 78% of the available oil while in test 2 only 70% was recovered to the retentate. Test 1 allowed 12.4% of the available oil to pass through to permeate with a total loss of 10% to the system, while test 2 only allowed transfer of 3.7% of the available oil into the permeate but showed a system loss of 27% oil. It appears that the MF filter itself retained more oil per unit area in test 2 than in test 1 which could have limited the efficiency of the MF filter.

Based on the above, the following describes the setup, filtration, analysis and mass balance of an evaluation with 0.65 um PVDF (polyvinylidene fluoride) M.F filter, including further processing through the UF membrane prior to spray drying. This feed material was generated in the continuous operation of the production plant at a ratio of 8:1 water to meal. As a result, there was no refrigeration step. Phytase was added at a rate of 1.2% of meal addition. The above description is an example of a suitable equipment, membrane size and membrane material. However, one skilled in the art, based on the teachings herein, will recognized that there are suitable alternatives which can provide similar results.

A 10 L sample was collected and processed (Pre Skimming/Pre HTST). The equipment used comprised:

Millipore Pellicon 2 Mini (0.65 um UPP-U0.1) microfiltration unit, Durapore Membrane, PVDF Material, 0.1 m$^2$ Membrane Area UF—Prep/Scale TFF 6 ft2 Cartridge, PTGC 10K Polyethersulphone, Pump—MasterFlex Model 77410-10 with a variable speed (33 to 650 rpm), and Centrifuge—Thermo Scientific CL-31.

Skimming—The material was centrifuged in 250 mL aliquots using the Thermo Scientific CL-31 centrifuge at 4000 rpm (2700 G) for 10 minutes. Any oily matter on the surface was pipetted off and settled solids were mixed back into solution for further processing. This provided approximately 8 liters of material for further processing.

Millipore Filtration—The solution after skimming was heated to 52° C. (±2) in 2 L aliquots. The pH of test liquid was 7.44.

Figure 2:
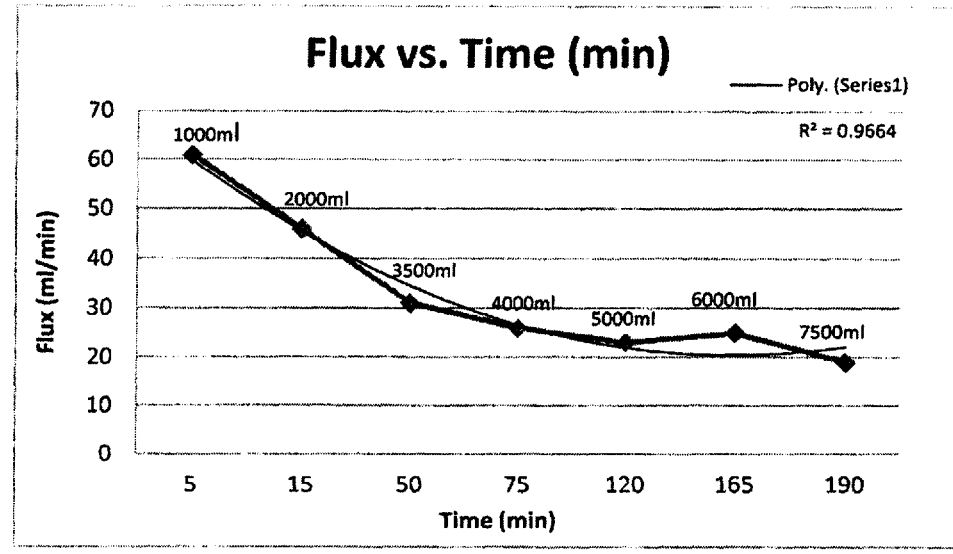
FIG. 2 is a graph showing the change in flux during ultrafiltration over operating time.

Permeate Rate (Flux)—FIG. 2 shows the change in flux over operating time, which is also a function of the volume processed. As expected, there was a significant reduction in Flux after processing the first 3.5 L and flux leveled off to approximately 20 mL/min while processing the last 4 L. Table 15 shows the Mass Balance (M.F) Volumes. A calculated loss of approximately 350 mL (4.6%) was due material lost in tubing, by evaporation on hotplate, etc.

TABLE 15

| MF Volumes | | |
|---|---|---|
| Feed material (Alpha Laval Disc) Skimmed | 7600 mL | 100.0% |
| M.F Retentate | 600 mL | 7.9% |
| M.F Permeate | 6650 mL | 87.5% |

Ultrafiltration/Diafiltration—The MF permeate described above was heated to approximately 35° C. and processed through the UF unit. a total volume of 6300 mL was processed through the UF unit and then diafiltered.

Spray Drier—Approximately 600 mL of material was spray dried and all sample fractions were collected for further analysis and processing. Liquids were tested for protein content and additional samples of known volume were dried in the oven at 90° C. prior to determining solids and oil content on a dry weight basis (dwb). The results are shown in Table 16.

TABLE 16

| TEST RESULTS | | | | | | | | |
|---|---|---|---|---|---|---|---|---|
| Sample Description | Vol Dried (mL) | % Solids (dwb) | % Protein (Liq) | % Protein (dwb) | % Oil (dwb)* | Oil (mg/ 100 mL) | Mass(g) of dry sample for oil analysis | mass of oil isolated (mg) |
| Process Solution | 455 | 3.78 | 1.50 | 38.0 | 13.8 | 52 | 3.0088 | 42 |
| Disc - Lab skimmed/centrifuged | 475 | 3.62 | 1.35 | 39.3 | 9.22 | 33 | 3.0112 | 28 |

TABLE 16-continued

TEST RESULTS

| Sample Description | Vol Dried (mL) | % Solids (dwb) | % Protein (Liq) | % Protein (dwb) | % Oil (dwb)* | Oil (mg/ 100 mL) | Mass(g) of dry sample for oil analysis | mass of oil isolated (mg) |
|---|---|---|---|---|---|---|---|---|
| Permeate from M.F - 0.65 | 135 | 2.71 | 1.17 | 38.6 | 0.53 | 1 | 1.0000 | 1 |
| Retentate From M.F - 0.65 | 405 | 10.23 | 4.00 | 40.6 | 28.8 | 295 | 3.0087 | 87 |

Mass Balance M.F (Proximate) Table 17 shows the balance of protein and oil from the MF process. Based on the calculated losses, 100% of the available soluble protein is accounted for in either permeate or retentate fractions. The soluble protein available was 91.6% of the total protein in the Alpha Laval feed material. Of this, 70% of the total available soluble protein was directly transferred to the permeate stream via MF filtration. In addition, by diafiltering the M.F retentate the recovered soluble protein could have been as high as 76.5 g of the 99.3 g available or 77.0% recovery. Another 3.8 g (5.0 g protein×77.0% recovery) of soluble protein can be transferred from the overall volume feed loss to the permeate fraction. Also, additional protein was removed by sampling 135 mL of permeate for oven drying, accounted for another 1.4 g of protein. Tests showed that the permeate fraction contained approximately 4% of the available oil which passed through the MF membrane to permeate while 70% of the oil was retained in the MF retentate. By calculating the potential oil loss via feed loss, additional 4% oil was accounted for. According to a mass balance, while only 78% of the total oil available from the feed liquid was recovered by mass balance, a large portion of the missing 22% (5.2 g) comprised oil retention on the MF filter.

TABLE 17

Mass Balance of MF (Proximate)

| Material | Protein (g) | Recovered Protein (wt %) | Oil (g) | Recovered Oil (wt %) |
|---|---|---|---|---|
| Feed (Lab Skimmed) | 108.4 | 100 | 25 | — |
| Feed Volume Losses[1] | | | | |
| Loss by Insoluble Protein[2] | 9.1 | 8.4 | — | — |
| Total available (Soluble) protein)[2] | 99.3 | 91.6 | | |
| MF Permeate | 69.5 | 70.0 | 1.0 | 4 |
| Lost to retentate stream[3] | 7.0 | 7.0 | — | — |
| Removed sample[4] | 1.4 | 1.4 | — | — |
| Feed Volume Losses[1] | 3.5 | 3.5 | — | — |
| Total Permeate including losses | 81.4 | 82.0 | 1.0 | 4 |
| MF Retentate[5] | 18.0 | 18.1 | 17.7 | 70 |
| Feed Volume Losses[1] | 1.1 | 1.1 | 1.1 | 4 |
| Total Retentate including losses | 19.1 | 19.2 | 18.8 | 74 |
| Total Recovered (Soluble) Protein (%) | | 101.3 | | 78 |

A small fraction of the retentate was collected and oven dried to determine the % solids on a dry weight basis; the remainder was spray dried.

TABLE 18

Proximate Analysis (Spray Dried)

| Sample Description | Vol Dried (mL) | % Solids | % Protein (dwb) | % Oil (dwb)* | Phytate |
|---|---|---|---|---|---|
| (Oven Dried) | 25 | 5.05 | Ave 93.7 | ND | ND |
| Retentate U.F Input (Spray dried) | — | — | 93.2 | 0.24 | 1.18 |

Protein Purity (Comparison)—The liquid feed stream was taken from the in-process production stream. The same material processed in the plant produced a purity of 79.1% (dwb); while the lab processed material produced a purity of >90% (93.2).

Amino Acid Profile (Comparison)—The following soluble amino acid comparison of the final product is standardized to 100% AA. The profile is substantially unchanged from that in the starting material.

TABLE 19

| | Production | Membrane Filtration - Laboratory (Spray Dried) |
|---|---|---|
| AMINO ACID PROFILE:. | | |
| Sulphur AA | 2.85 | 3.93 |
| Aromatic AA | 5.43 | 6.41 |
| BCAA | 11.71 | 14.36 |
| AAS | 1.09 | 1.01 |
| Amino Acid Profile - 18 primary [g AA/100 g protein] | | |
| Aspartic Acid | 9.92 | 9.59 |
| Glutamic Acid | 18.66 | 20.54 |
| Serine | 5.39 | 5.27 |
| Glycine | 5.81 | 5.84 |
| Histidine | 3.38 | 3.01 |
| Arginine | 7.44 | 7.64 |
| Threonine | 4.93 | 4.23 |
| Alanine | 4.75 | 4.81 |
| Proline | 5.35 | 5.93 |
| Tyrosine | 3.76 | 3.41 |
| Valine | 5.11 | 4.84 |
| Methionine | 2.33 | 2.28 |
| Cystine | 1.64 | 2.01 |
| Isoleucine | 3.96 | 3.69 |
| Leucine | 7.24 | 7.16 |
| Phenylalanine | 3.80 | 3.60 |
| Lysine | 5.22 | 4.84 |
| Tryptophan | 1.35 | 1.31 |
| Total Amino Acids | 100.00 | 100.00 |

Visual Observations

Figure 3:
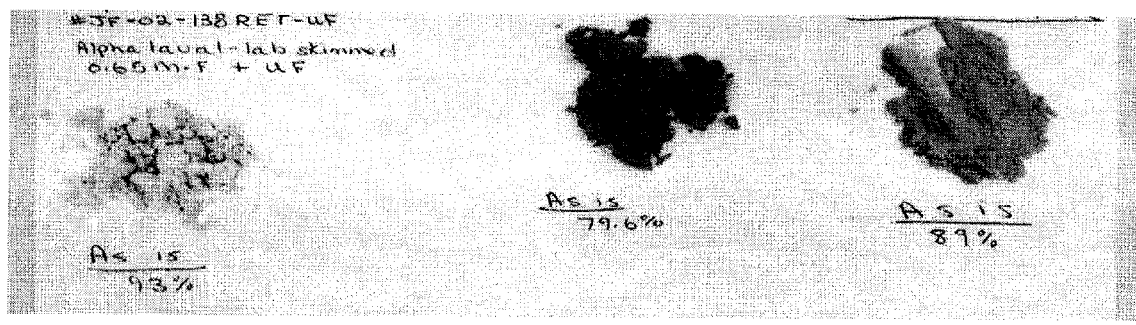
FIG. 3 is a photograph showing the lab processed/spray dried powder compared to two prior lots of continuously produced protein.

FIG. 3 is a photograph comparing the visual image of the lab processed/spray dried powder compared to two prior lots of continuously produced protein. The laboratory spray dried product is clearly lighter in color with a more powdery consistency.

Based on the data obtained from the Millipore filter evaluations described above, the 0.65 um filter was found to be the best in generating a high flux rate and allowing protein permeation through the filter while retaining oil on the feed side of the system. In addition, it was concluded that the use of Millipore microfiltration improves the achievable protein purity as is seen by comparing the spray dried material from this experiment at 93.2% (dwb) to the purity of the in-plant generated material at only 79.6% protein. However, based on this data a 0.4-0.8 um filter, dependent on actual in-use performance, will be used in the continuous process. Attached as FIGS. 4 A and B, which represent a single process flow diagram, is a schematic diagram showing the various steps in separating canola press cake into the insoluble and soluble portions to produce a) an isolate comprising a high concentration of soluble canola proteins, b) a non-protein, soluble phase comprising primarily sugars, and a wet meal comprising insolubles, those insoluble being primarily insoluble proteins.

The operating conditions set forth in FIGS. 4A and B were chosen based on the various evaluations set forth above. The feed material was a crushed canola seed with approximately 14% oil prepared by the cold pressing process described above. To show the benefit of microfiltration, the product out of ultrafiltration and the spray dryer with, and without microfiltration, based on prior data, is projected to be as listed in Table 20. MF1 is provided as a filter for the liquid stream from the skimmer. MF2 is provided to filter and recover soluble protein from wash water used to clean the internal surfaces of the processing equipment and vessels. Table 21 provides a comparison of the molecular weight distribution of the dry spray dried product, with and without MF, and the actual measured soluble protein and residual oil concentration on a moisture free basis. The PDI is substantially unchanged from that of the pressed cake shown in Table 2. It should be noted that removing residual moisture from the spray dried product provides a protein concentration of at least 93%.

TABLE 20

PROJECTED ISOLATE PROPERTIES

| | | WITHOUT MF | | WITH MF |
| --- | --- | --- | --- | --- |
| UF RETENTATE | Fibre/Cellulose | 2.00% | Fibre/Cellulose | 0.00% |
| | Soluble Protein | 12.00% | Soluble Protein | 11.00% |
| | Insoluble Protein | 2.00% | Insoluble Protein | 0.00% |
| | Soluble Carbs | 0.90% | Soluble Carbs | 0.90% |
| | Ash | 0.40% | Ash | 0.04% |
| | Oil | 0.40% | Oil | 0.00% |
| | Water | 82.6% | Water | 87.6% |
| SPRAY DRY (INCLUDES MOISTURE) | Fibre/Cellulose | 10.7% | Fibre/Cellulose | 0.0% |
| | Soluble Protein | 64.2% | Soluble Protein | 86.7% |
| | Insoluble Protein | 10.7% | Insoluble Protein | 0.0% |
| | Soluble Carbs | 4.8% | Soluble Carbs | 6.8% |
| | Ash | 2.1% | Ash | 0.3% |
| | Oil | 2.1% | Oil | 0.0% |
| | Water | 5.3% | Water | 6.1% |

TABLE 21

| SPRAY DRIED PRODUCT | | |
| --- | --- | --- |
| Molecular Mass [kDa] | (no MF) | (MF) |
| 300 | 26% | 26% |
| 300-50 | 5% | 6% |
| 50-30 | 4% | 5% |
| 30-10 | 15% | 20% |
| 10-5 | 25% | 22% |
| <5 | 23% | 18% |
| Protein purity (dwb) | 79% | 93% |
| Oil | 4% | 0.24% |

EXAMPLE 6

The following example is a general process for the protein products produced in Example 7-10.

Canola seed was cold pressed to achieve oil levels of ca. 12% in the meal, but with retention of the native solubility of the protein (PDI=>30) as a result of not using elevated temperatures. Canola meal (850 kg) was added to water (7000 L) at 50±5° C. under good agitation. The pH was adjusted to 5±0.2 with food-grade citric acid (or any other food-grade acid). Food-grade Phytase (1.2% v/w (meal)) and Validase (0.1% w/w (meal)) was added and the slurry was mixed for 1-2 hours. The pH was then adjusted to 7 with sodium hydroxide (or any other food-grade base). Following pH adjustment, additional water was optionally added to achieve the desired solids level (v/v). In this case 30% solids (v/v) was targeted by the addition of 2400 L of water. The aforementioned process is repeated to generate a desired volume of slurry.

The solids were removed from the liquid phase using a continuous decanter centrifuge at about 3000 G and two disk stack continuous centrifuges, in series (8300 G and >10,000 G, respectively). The clarified (i.e. solids removed) liquid was then processed through a third continuous disk stack centrifuge (>6000 G) designed to remove oil from the aqueous phase. The processing temperature through the decanter centrifuge is maintained below 20° C. The processing temperature through all of the disk stacks was maintained above 50° C.

The clarified, de-oiled aqueous phase was then treated by HTST (high temperature short-time pasteurization) (72-74° C.) for microbiological control and safety and then processed through a continuous ultrafiltration/diafiltration, which separates the sugars, ash, and impurities from the proteins and concentrates the proteins. The resulting concentrated protein solution is spray dried.

Seed Studies

In one embodiment, the processes of the present disclosure are useful for processing canola seed and canola meal, rapeseed, mustard seed, broccoli seed, flax seed, cotton seed, hemp seed, safflower seed, sesame seed and soybean meal, can be processed in the same manner to provide high protein content end products.

In one embodiment of the disclosure, the seed source comprises canola seed or canola meal, for example, *Brassica juncea* or *Brassica napus*.

EXAMPLE 7

*B. napus* was evaluated as the seed source. *Napus* seed has slightly higher levels of protein (21-24%) to *juncea*, and a significantly higher PDI (25-30 *juncea* vs. 35-40 *napus*).

Napus was processed according to the present disclosure and found to have the following amino acid profile as shown in Table 22:

TABLE 22

|  | Run 1 | Run 2 | Run 3 | Run 4 |
| --- | --- | --- | --- | --- |
| Aspartic Acid | 7 | 6.88 | 6.66 | 6.67 |
| Glutamic Acid | 16.4 | 17.3 | 18.4 | 18.6 |
| Serine | 3.86 | 4.07 | 3.92 | 3.79 |
| Glycine | 4.02 | 4.23 | 4.18 | 4.12 |
| Histidine | 2.39 | 2.73 | 2.84 | 2.65 |
| Arginine | 5.72 | 5.94 | 6.09 | 5.97 |
| Threonine | 3.51 | 4.06 | 3.57 | 3.34 |
| Alanine | 3.57 | 3.69 | 3.60 | 3.54 |
| Proline | 4.92 | 5.4 | 5.60 | 5.60 |
| Tyrosine | 2.31 | 2.39 | 2.36 | 2.32 |
| Valine | 3.88 | 3.98 | 3.89 | 4.00 |
| Methionine | 1.73 | 2.03 | 1.88 | 1.88 |
| Cystine | 1.98 | 2.42 | 2.58 | 2.70 |
| Isoleucine | 3.18 | 3.14 | 3.12 | 3.57 |
| Leucine | 5.82 | 5.89 | 5.77 | 6.41 |
| Phenylalanine | 3.49 | 3.43 | 3.30 | 3.22 |
| Lysine | 4.8 | 5.46 | 5.27 | 5.48 |
| Tryptophan | 1.08 | 1.12 | 1.14 | 1.20 |
| Total Amino Acids | 79.7 | 84.2 | 84.2 | 85.1 |

Additionally, all 4 lots of *napus* tested <2% oil (ST).

EXAMPLE 8

The effect of the dilution of the seed meal with water, with a range of 1:5 to 1:14 was examined for its overall influence on product yield and purity. Increasing the dilution ratio has the consequence of requiring more water which also lowers the amount of solids leaving ultrafiltration. Ultrafiltration works on the principle of volume and volume reduction—and increased solids in the UF show up as flux reduction over time.

At a dilution of 1:10 of aqueous solvent to oilseed meal, the following amino acid profile of the protein product was obtained as shown in Table 23:

TABLE 23

|  | Run 1 |
| --- | --- |
| Aspartic Acid | 6.93 |
| Glutamic Acid | 19 |
| Serine | 4.33 |
| Glycine | 4.33 |
| Histidine | 2.96 |
| Arginine | 6.16 |
| Threonine | 3.65 |
| Alanine | 3.72 |
| Proline | 6.02 |
| Tyrosine | 2.32 |
| Valine | 4.17 |
| Methionine | 1.97 |
| Cystine | 2.58 |
| Isoleucine | 3.41 |
| Leucine | 6.31 |
| Phenylalanine | 3.6 |
| Lysine | 5.37 |
| Tryptophan | 1.22 |
| Total Amino Acids | 88.1 |

Once the oilseed meal was mixed with the aqueous solvent and optionally mixed with phytase and adjusted for pH, the mixture was processed in a decanting centrifuge. The decanting centrifuge was mostly unaffected by the dilution ratio used. At lower speed (ca. 50 liters per minute) there was ca. 4% solids in the centrate, which increases to 5% as the speed is increased 110 lpm (all at <20° C.).

The centrate from the decanting centrifuge was then transferred to two (in series) disc stack centrifuges. Both disk stacks (Disk Stack 1 (DS1)—Alpha Laval Brew 2000; Disk Stack 2 (DS2)—Westphalia CSA160) were minimally affected by the change in dilution. The centrifuges were operated at slightly slower speeds to stay in specification (DS1<1.5%, DS2<0.2%). DS1 could be ramped to 90 lpm at which point it began to eject more solids than specification. Accordingly, DS2 had to be slowed down because it was overwhelmed. Staying below 1.5% solids on DS1 allows one to achieve <0.2% solids on DS2.

The centrate obtained from the disc stack centrifuges was then subjected to an oil skimming centrifuge. The skimmer (Westphalia MSE500) was unaffected by the change in dilution ratio. There were no performance indicators that did not meet specification. The skimmer was run at 300 lpm with a discharge of 2.5-3%. The oil side reject was 40-60% oil emulsion, generally averaging below 50%.

Subsequent to the skimming centrifuge, the centrate was then subjected to ultrafiltration. The centrate was subjected to ultrafiltration for 6 hours, wherein the brix reading on the UF retentate climbed to 26—typically the brix level on the UF would be 19-21—indicating increased % solids, as expected. The change in dilution (about 20%) increased the maximum brix observed by a similar amount, as would be expected. $P_{max}$ was attained after 4 hours of processing time. $P_{max}$ generally occurs 5-7 hours after starting production. Again, as expected, this provides more evidence of increased solid levels in the centrate, and accordingly, the overall process is simply adjusted to take into account the increased solids. In addition, due to the reduced dilution, the amount of solution to process fell accordingly, which contributed to not having to put the UF in recycle or stop production at any point.

The adjustment of the dilution level did not affect spray drying. The bulk density of the spray dried product was 0.273. *Napus* has returned bulk densities of 0.193-0.263: the bulk densities will vary based on solids in the feed. In general terms, *napus* delivers, on average, higher bulk densities than *juncea* (>0.2). The density for this example was 0.39, which again is slightly higher than diluted lots (0.36-0.37) and higher than *juncea* (typically <0.3).

Temperature Studies

In one embodiment, the temperature of any of the phases (i.e. liquid phase, solid phase) produced during the processes of the present disclosure are adjusted at any point during the process. For example, in one embodiment, the liquid phase (after separation of the slurry) is heated to a temperature between 30° C. and 70° C., or between 40° C. and 60° C., or about 50° C., before being subjected to a liquid separation (such as in the disc stack and/or skimming centrifugation process). In another embodiment, the temperature of the slurry subjected to the separation (for example, decanting centrifuge) is greater than 0° C. but less than 20° C., or between 10° and 20° C., or about 20° C.

EXAMPLE 9

A heat exchanger was installed before Disk Stack 1 (DS1—Alpha Laval Brew 2000). This heat exchanger (a plate and frame) used water as heating media and was able to increase the temperature of the process solution from about 13° C. (as received from the decanting centrifuge) to about 50° C. prior to feeding the product to the Disk Stacks centrifuges. The starting dilution ratio of aqueous solvent to meal was 12.5:1 (w/w). The following amino acid profile of the protein product was obtained as shown in Table 24:

TABLE 24

|  | Run 1 |
| --- | --- |
| Aspartic Acid | 6.83 |
| Glutamic Acid | 19.2 |
| Serine | 4.11 |
| Glycine | 4.2 |
| Histidine | 2.83 |
| Arginine | 6 |
| Threonine | 3.4 |
| Alanine | 3.64 |
| Proline | 5.72 |
| Tyrosine | 2.32 |
| Valine | 4.2 |
| Methionine | 1.97 |
| Cystine | 2.6 |
| Isoleucine | 3.32 |
| Leucine | 6.17 |
| Phenylalanine | 3.51 |
| Lysine | 5.5 |
| Tryptophan | 1.31 |
| Total Amino Acids | 86.8 |

The decanting centrifuge processed the solution at 16-18° C. Solids carryover was 3-5% (average of 4%) at 60-100 lpm. In addition, the speed of the decanting centrifuge was increased to 100 lpm for a period of time to test solids carryover, which still generated 5% insoluble solids carryover.

In changing the temperature as the liquid phase entered DS1, it was noted that the insoluble solids declined from 4-5% to ca. 2% in the feed to DS1. This indicates a temperature-dependent compaction of the insoluble solids.

At the outset, DS1 was started at 120 lpm with a 3 min shoot rate. Both the speed and the timing between shots were increased incrementally. The feed rate was increased to a maximum of 170-180 lpm where 0.5-0.8% insoluble solids was attained: at lower rates (≤140 lpm), the insoluble solids fell to trace to 0.1%. This indicates that DS1 attains low levels of solids. Concurrent to the increase in feed rates, the shot interval was changed from 3 min to 5 min. DS1 produced shots (insolubles) which had higher viscosities, as opposed to slightly loaded process solution (water-like consistency). Overall, there was a 50% to 80% increase in capacity through DS1 with a substantial increase in prospective yield (higher flowrate and reduced amount of shots.

Similarly, DS2 could also be run much faster with longer intervals between shoots. Up to 170 lpm (ca. 50° C.), DS2 provided <0.2% insoluble solids. The shot interval was increased to 8 min without degradation of centrate quality.

The centrate from the decanting centrifuge had ca. 4% solids, while the feed to DS1 was half that (ca. 2%). The change in solids level between the decanting centrifuge is attributed to solids compaction due to heating in the heat exchanger prior to entry to the disc stack centrifuge. In addition, the clarity of the solution was improved with heating the solution to >50° C. prior to centrifugation.

The increase in temperature of the solution to the skimming centrifuge resulted in no substantive changes. In general terms, there was a bias towards oil emulsion in the oil-side reject. The levels were 30-70%, but the average values were much above 50% oil emulsion in the spin downs.

During ultrafiltration (for approximately 9 hours), the brix level climbed as high as 26, but was generally between 20 and 22. $P_{max}$ was achieved approximately 5 hours after starting the run.

There were no substantive changes during the spray drying process.

EXAMPLE 10

Increasing the temperature of the total process was then examined. The following amino acid profile of the protein product was obtained as shown in Table 25:

TABLE 25

|  | Run 1 |
| --- | --- |
| Aspartic Acid | 6.99 |
| Glutamic Acid | 17.9 |
| Serine | 4.15 |
| Glycine | 4.23 |
| Histidine | 2.7 |
| Arginine | 6.02 |
| Threonine | 3.5 |
| Alanine | 3.61 |
| Proline | 5.57 |
| Tyrosine | 2.37 |
| Valine | 4.11 |
| Methionine | 1.88 |
| Cystine | 2.34 |
| Isoleucine | 3.36 |
| Leucine | 6.16 |
| Phenylalanine | 3.59 |
| Lysine | 4.83 |
| Tryptophan | 1.19 |
| Total Amino Acids | 84.5 |

During the course of this run, the decanting centrifuges were operated at 80-100 lpm at about 50° C., with the average rate being 90 lpm. The solids in the centrate ranged from 2-4.5% with the average level of solids in the centrate (for both machines) being 3.5%. The variation in solids in the centrate to as low as 2% was not due to improved efficiency, but was most likely due to variations in feed solids: concurrent to the low observed result, the feed solids dropped to 25% indicated a 90% efficiency rate. This efficiency rate is not materially different from the efficiency rate observed when the decanters were run with feed at <20° C. In general terms, the operation of the decanting centrifuge is not materially affected by the operating temperature.

The two disk stack centrifuges in series worked as expected. DS1 (about 190 lpm) produced approximately 1% solids while DS2 (about 155 lpm) reduced the process stream to <0.2% solids (typically 0.1%-trace). The shoot rates were 5 and 8 minutes, respectively.

There was no compaction of solids noted between the heat exchanger and DS2 because the compaction temperature had already been reached when the process stream was passed through the decanting centrifuge.

During skimming centrifugation, spin downs of the protein phase showed no oil and the spin down of the oil phase showed 29-50% oil emulsion.

The increased temperature of the process did not affect the spray drying process.

Table 26 illustrates the processing information from Examples 7-9:

TABLE 26

|  | Example 8 | Example 9 | Example 10 |
|---|---|---|---|
| Dilution (water to meal) | 10:1 | 12.5:1 | 12.5:1 |
| Processing condition | Normal (cold) | Cold in decanting centrifuge (normal) and hot through disk stack centrifuges | Hot throughout decanting and disk stack centrifuges |
| Protein | 92.7% dwb [88.3% as is] | 96.6% dwb [91.7% as is] | 89.7% dwb [85.5% as is] |
| Oil (Swedish tube) | 1.32% | 0.73% | 2.21% |
| Decanter centrate % solids (v/v) | 4-5% (18-19° C.) | 3-5% (16-18° C.) | 2-4.5% [3.5% avg] (ca. 50° C.) |
| Decanter run rate | 80-100 lpm [[avg 90] | 60-100 lpm | 80-100 lpm [avg 90] |
| DS1 feed % solids (v/v) | 4-5% | 2% (heating from 13° C. to ca. 50° C.) | 2-4.5% [3.5% avg] (ca. 50° C.) |
| DS1 centrate % solids (v/v) | <1.5% | 0.5-0.8% | 1% |
| DS1 run rate | 90-100 lpm | 170-180 lpm | 190 lpm |
| DS2 centrate % solids (v/v) | <0.2% | <0.2% | 0.1%-trace |
| DS2 run rate | 90-100 lpm | 170 lpm | 155 lpm |

As shown in Table 26, decantation efficiency is largely unaffected by temperature. Compaction of solids occurs when the process solution is heated following decantation at <20° C. to about 50° C. or higher. The solids compaction allows for increased removal of insoluble solids via the disk stack centrifuges, which allows the disk stacks to run faster and shoot less often. The disk stack centrifuges run more efficiently at higher temperature as more throughput and higher yield can be obtained when the disk stacks are run at higher temperature.

With respect to the oil skimming centrifuge, the amount of oil present in the protein product is lower when the process solution is heated going to the disk stack centrifuge. This can be due to several possibilities: 1) higher clearance of oil through the skimmer at elevated temperature; or, 2) higher clearance of oil due to improved insoluble solids removal at elevated temperature (improved solution clarity; it is known that the insoluble solids carry a significant amount oil—see Table 27, specifically data for the "less dense solid layer").

TABLE 27

| Layer | Protein % (dwb) | Oil % (dwb)* |
|---|---|---|
| Supernatant (liquid layer) | 44 | 4.7 |
| Less dense solid layer | 43 | 15.2 |
| More dense solid layer | 29 | 9.3 |

*determined by soxhlet extraction

As expected, the UF reached $P_{max}$ sooner for example 8 (with higher solids being fed to the UF). This is due to the increased solids fed to the UF as a direct result of the reduced dilution. The flux results for Examples 8-10 are shown in Table 28:

TABLE 28

|  | Example 8 | Example 9 | Example 10 |
|---|---|---|---|
| Dilution (water to meal) | 10:1 | 12.5:1 | 12.5:1 |
| Processing condition | Normal (cold) | Cold in decanting centrifuge (normal) and hot through disk stack centrifuges | Hot throughout decanting and disk stack centrifuges |
| Time Started | 1300 | 2220 | 1300 |
| Time ended | 1900 | 1815 | 0530 |
| Total run time (hours) | 6 | 10.3 | 10 |
| Starting flow rate (m3/hr) | 11.0 | 12.5 | 13.0 |
| Ending flow rate (m3/hr) | 9.55 | 8.3 | 10.1 |
| Time to $P_{max}$ (hours) | 4 | 60-100 lpm | 80-100 lpm [avg 90] |
| VCF | 20 | 20 | 20 |
| Brix | 18-26 | 17-22 | 17-24 |

The overall yields results for Examples 6-9 are shown in Table 29:

TABLE 29

|  | Example 7 (Run 3) | Example 8 | Example 9 | Example 10 |
|---|---|---|---|---|
| Cake processed (kg) | 17000 | 8500 | 9350 | 10200 |
| Protein powder obtained (kg) | 1411 | 468 | 792 | 723 |
| Yield on cake | 8.3% | 5.5% | 8.47% | 7.1% |

Example 9 demonstrates an overall yield of approximately 8.5% purified protein. The reason for the increased yield is due in part to the increased flow rate and decreased frequency of "shootings" (machine discharges to remove accumulated solids). These shootings remove process solution, roughly equivalent to the volume of the bowl, and therefore, reduced shootings results in higher yield. Therefore, the disk stacks can be run faster and with longer intervals between shoots. This is due to improved solids compaction at higher temperature in addition to reduced viscosity and density of the process solution: the density and viscosity of the solids phase is assumed to be unchanged by the temperature increase making them heavier relative to the liquid phase, therefore easier to separate.

The protein isolates prepared in the above examples were then examined for their molecular weight profiles, as shown in Table 30.

TABLE 30

| Mass (kDa) | B. Juncea | B. Juncea | B. Napus | B. Napus |
|---|---|---|---|---|
| | | % | | |
| >300 | 48 | 61 | 54 | 44 |
| 300-50 | 2 | 2 | 2 | 2 |
| 50-30 | 2 | 2 | 2 | 2 |
| 30-10 | 11 | 13 | 30 | 39 |
| 10-5 | 27 | 18 | 7 | 8 |
| <5 | 8 | 2 | 5 | 3 |

The molecular weight profile of the protein isolates prepared in accordance with the processes of the present disclosure demonstrate that both cruciferin and napin proteins are present in the isolates. In one embodiment therefore, there is a protein isolate comprising:

i) a first portion of proteins having a molecular weight of above about 300 kDa, wherein the first portion represents between 40 and 65% of the total protein;

ii) a second portion of proteins having a molecular weight of between about 300-50 kDa, wherein the second portion represents between 0 and 5% of the total protein;

iii) a third portion of proteins having a molecular weight of between about 50-30 kDa, wherein the third portion represents between 0 and 5% of the total protein;

iv) a fourth portion of proteins having a molecular weight of between about 30-10 kDa, wherein the fourth portion represents between 10 and 40% of the total protein;

v) a fifth portion of proteins having a molecular weight of between about 10-5 kDa, wherein the fifth portion represents between 5 and 30% of the total protein;

vi) a sixth portion of proteins having a molecular weight of less than about 5 kDa, wherein the sixth portion represents between 0 and 10% of the total protein.

The smaller portions are probably assay artifacts. The proteins are multimeric and one part of them drops off to make 2 smaller fragments.

Hydrolyzed Concentrate

Enzymatic hydrolysis was previously performed (applicant's prior parent applications cited above) using a precursor comprising defatted canola meals containing less than 3% oil (dwb) to produce a hydrolyzed protein concentrates. These prior hydrolyzed protein concentrates typically contained 75-90% (dwb) protein. It has now been discovered that high quality hydrolyzed protein concentrates can be produced from high oil materials (Meal containing >9% oil (dwb) referred to herein as "oily meal), and also commonly referred to as canola press cake, obtained by pressing the meal to remove a portion of the oil, the meal not being exposed to solvent extraction. It was found that the residual oil can be liberated from the meal as part of or after the hydrolysis process. Further, it has been found that subsequent ultrafiltration (UF) would remove any oil liberated from the meal and therefore, the use of the oily meal as an input into the hydrolysis process has viability. Unexpectedly, it was discovered that applicant's previously disclosed process that was performed on defatted meal provided an equal or better product when an oily meal was the feed stream and that variability in incoming feed streams does not impact the process and the quality of the hydrolyzed end product.

Examples 11-13 below describe laboratory scale tests conducted to evaluate the effect of several variables and several different enzymes on the hydrolysis of insoluble proteins to form and then separate soluble proteins and peptides. Alcalase® and Flavourzyme®, examples of endopeptidases and exopeptidases, are members of a large group of enzymes that catalyze the hydrolysis of peptide bonds in the middle or at the terminal amide linkages of a polypeptide chain or protein molecule. Neutrase® and Protamex® are more broadly classified as is a protease enzymes. To demonstrate a worst case scenario, the feed material entering the hydrolysis process was an oily meal having about 10.5% dwb oil that would, which is greater than the 9 to 9.5% (dwb) oil typically found in a press cake. Flavourzyme®, Neutrase®, Protamex®, and Alcalase® are registered trademarks of Novozymes A/S of Krogshoejvej, Denmark.

EXAMPLE 11

Processing of Oily Meal

Materials

Feed material—high oil insoluble solids separated and recovered as a side product in the process to produce protein isolate from *B. juncea*.

Enzyme—Alcalase 2.4 L FG and Flavourzyme 1000 L were obtained from Novozymes North America, Inc., Franklinton, N.C. USA.

Procedure

Approximately 0.4 kg of the insoluble solids was mixed for 10 minutes under agitation with 1.2 kg of distilled water and then subjected to centrifugation at 4,000 RPM for 10 minutes, separating a $1^{st}$ washed insoluble solids from a liquid extract. The $1^{st}$ washed solids was then mixed for 10 minutes under agitation, with 1.2 kg of distilled water and then subjected to centrifugation at 4,000 RPM for 10 minutes to separate a $2^{nd}$ washed solids (0.38 kg) from the liquid extract.

The $2^{nd}$ washed solids were then mixed with distilled water at a solids to water ratio of 1 to 2.5 by weight. The pH was adjusted to 8.3 and temperature adjusted to 60° C. under agitation. One gram of Alcalase (0.25% dosage based on 0.4 kg of starting weight high oil solids (oily meal)) was added to the slurry and maintained at 60° C. for 4 hours to cause hydrolysis. The slurry was then cooled to 50° C.; the pH was measured to be 6.75. One gram of Flavourzyme (0.25% dosage based on 0.4 kg of starting weight of high oil solids (oily meal)) was added and additional hydrolysis was conducted at 50° C. for 4 hours.

After hydrolysis, the slurry was centrifuged at 4,000 RPM for 10 minutes to separate the soluble hydrolyzed protein extract from the insoluble solids. The insoluble solids were mixed with water at a solids-to-water ratio of 1 to 2 by weight, which was followed by centrifugation to separate additional soluble extract from the washed solids. The soluble hydrolyzed protein extracts were combined together and approximately 1.6 kg of the combined hydrolyzed protein extract was obtained. The combined soluble hydrolyzed protein extract was filtered through a 10,000 dalton molecular weight cut-off UF membrane. The permeate (filtered hydrolyzed protein extract) was analyzed for protein and solids content.

Results and Discussion

The results are showed in Table 31 below:

TABLE 31

Analysis of Starting and Intermediate Material and Resultant Hydrolyzed Protein Extract and Solids.

| Sample | Moisture (%) | Protein (%, dwb) | Ash (%, dwb) | Oil (%, dwb) | Crude Fiber (%, dwb) |
|---|---|---|---|---|---|
| Insoluble Solids (Feed material) | 80.50 | 32.8 | 5.62 | 10.5 | 15.3 |
| Combined Hydrolyzed Protein Extract | 99.02 | 79.6 | — | — | — |
| Membrane Filtered Hydrolyzed Protein Extract | 99.52 | 88.2 | 5.06 | 0.02 | 0.06 |
| Fiber Solids from Protein Hydrolysis | 87.5 | 14.6 | 5.2 | 10.7 | 23.9 |

The hydrolyzed protein extract before membrane filtration contains 80% protein on a dry weight basis. The protein recovery yield is 49%, which is calculated as the amount of proteins in the hydrolyzed protein extract divided by the amount of proteins in the starting solids. The membrane filtered hydrolyzed protein extract contains 88% protein on a dry weight basis. These results are comparable to those of hydrolyzed protein concentrate from defatted canola meal in the above referenced parent applications. This testing also shows that purity is improved (pre-UF 80%, post-UF 88%) by the UF process which removes fine particles and oily matter.

While the starting high oil solids material contained 10.5% oil, after membrane filtration, the filtered hydrolyzed protein extract contained 0.02% oil. Therefore, it was demonstrated that hydrolyzed protein concentrate containing high protein and little oil content can be produced from high oil meal using the process developed for defatted meal.

EXAMPLE 12

Evaluation of Enzyme Dosage

Aliquots of the $2^{nd}$ washed solids were exposed to different concentrations of enzymes hydrolysis time and enzyme combinations to evaluate the effect on protein recovery yield, purity and molecular weight distribution. Samples of the $2^{nd}$ washed solids were mixed with distilled water to prepare a slurry with about 8% solids, the pH of the slurry was adjusted to 8.3 and slurry was heated to 60° C. under agitation. Alcalase was added at a dosage based on the dry weight of the substrate. Hydrolysis was conducted at 60° C. for 4 hours. After protein hydrolysis, the slurry was centrifuged at 4,000 RPM for 10 minutes to separate the soluble hydrolyzed protein extract from the wet solids. The wet solids were washed with distilled water at a ratio of 1 to 2.5 by weight, which was followed by centrifugation at 4,000 RPM for 10 minutes to separate additional soluble hydrolyzed protein extract from the spent solids. The soluble hydrolyzed protein extracts were combined and the weight, solids and protein content were determined.

Alcalase—Alcalase dosage was 0.75% or 1.5% based on the solids dry weight.

Alcalase and Flavourzyme Combination—The slurry was cooled to 50° C. and Flavourzyme at a dosage based on the dry weight of the substrate (dry weight of the $2^{nd}$ washed solids) was added to the slurry and additional hydrolysis was conducted at 50° C. for 4 hours.

Alcalase and Neutrase Combination—The slurry was cooled to 50° C. and pH adjusted to 6.5. Neutrase at a dosage based on the dry weight of the substrate (dry weight of the $2^{nd}$ washed solids) was added to the slurry and additional hydrolysis was conducted at 50° C. for 4 hours.

Alcalase and Protamex Combination—The slurry was cooled to 40° C. and pH adjusted to 6.0. Protamex at a dosage based on the dry weight of the substrate (dry weight of the $2^{nd}$ washed solids) was added to the slurry and additional hydrolysis was conducted at 40° C. for 4 hours.

Results and Discussion

The results for the effect of enzyme and enzyme combination on protein recovery yield and purity of the hydrolyzed protein extract are shown in Table 32. These are representative examples of enzymes, combinations of enzymes, concentrations and treatment times. One skilled in the art will recognize that alternative enzymes can be used and the time and concentration can be varied so as to vary the degree of hydrolysis and the amino acid and peptide composition of the end product and the molecular weight distribution in that end product.

TABLE 32

Effect of Enzyme and Enzyme Combination on Protein Recovery Yield and Purity of the Hydrolyzed Protein Extract.

| Enzymes and Enzyme Combinations | Hydrolysis Time (Hour) | Protein Content of Hydrolysed Extract (%, dwb) | Protein Recovery Yield (%) |
|---|---|---|---|
| 0.75% Alcalase | 2 | 75.2 | 47.1 |
| 0.75% Alcalase | 3 | 73.7 | 49.0 |
| 0.75% Alcalase | 4 | 74.8 | 50.5 |
| 0.75% Alcalase | 8 | 74.2 | 59.8 |
| 1.5% Alcalase | 2 | 76.7 | 49.1 |
| 1.5% Alcalase | 3 | 75.4 | 53.2 |
| 1.5% Alcalase | 4 | 74.5 | 54.0 |
| 1.5% Alcalase | 8 | 74.0 | 61.6 |
| 0.75% Alcalase & 0.2% Flavourzyme | 4 for each enzyme | 74.5 | 61.2 |
| 0.75% Alcalase & 0.4% Flavourzyme | 4 for each enzyme | 72.2 | 59.0 |
| 0.75% Alcalase & 0.75% Flavourzyme | 4 for each enzyme | 71.7 | 59.4 |
| 1.5% Alcalase & 0.2% Flavourzyme | 4 for each enzyme | 71.2 | 60.1 |
| 1.5% Alcalase & 0.4% Flavourzyme | 4 for each enzyme | 74.7 | 64.8 |
| 1.5% Alcalase & 0.75% Flavourzyme | 4 for each enzyme | 74.3 | 65.3 |
| 1.5% Alcalase & 1.5% Flavourzyme | 4 for each enzyme | 72.9 | 62.2 |
| 0.75% Alcalase & 0.2% Neutrase | 4 for each enzyme | 74.5 | 63.8 |
| 0.75% Alcalase & 0.4% Neutrase | 4 for each enzyme | 74.9 | 63.4 |
| 1.5% Alcalase & 0.2% Neutrase | 4 for each enzyme | 75.9 | 66.4 |

TABLE 32-continued

Effect of Enzyme and Enzyme Combination on Protein
Recovery Yield and Purity of the Hydrolyzed Protein Extract.

| Enzymes and Enzyme Combinations | Hydrolysis Time (Hour) | Protein Content of Hydrolysed Extract (%, dwb) | Protein Recovery Yield (%) |
|---|---|---|---|
| 1.5% Alcalase & 0.4% Neutrase | 4 for each enzyme | 74.9 | 67.0 |
| 0.75% Alcalase & 0.2% Protamex | 4 for each enzyme | 76.0 | 57.2 |
| 0.75% Alcalase & 0.4% Protamex | 4 for each enzyme | 73.8 | 61.0 |
| 1.5% Alcalase & 0.2% Protamex | 4 for each enzyme | 70.3 | 63.2 |
| 1.5% Alcalase & 0.4% Protamex | 4 for each enzyme | 69.6 | 61.1 |

The protein recovery yield is calculated as the total proteins in the soluble hydrolyzed protein extract divided by the total proteins in the starting washed solids. Using 0.75% Alcalase, increasing the hydrolysis time from 2 to 8 hours enhances the protein recovery yield from 47.1% to 59.8%. Likewise, at 1.5% Alcalase, and an increase in the hydrolysis time from 2 to 8 hours enhances the protein recovery yield from 49.1% to 61.6%. However, the increase in Alcalase dosage from 0.75% to 1.5% only marginally improved protein recovery yield; hydrolysis time had a greater impact on yield than did concentration.

At 0.75% Alcalase, the additional use of Flavourzyme at 0.2-0.75% dosage was not found to improve the protein recovery yield and an increase in Alcalase amounts, Flavourzyme at 0.2-1.5% dosage only improved the protein recovery yield slightly. On the other hand, its use did improve the taste and reduce the bitterness of the hydrolyzed protein extract.

In contrast to Flavourzyme, the use of Neutrase at 0.2-0.4% dosage following the use of 0.75% Alcalase enhances the protein recovery yield to 62.2-63.8%; the protein recovery yield was increased even further to 66.4-67.0% following the use of 1.5% Alcalase. Thus, Neutrase improves the protein recovery yield by 4-9% over Alcalase alone, depending on the Alcalase dosage.

The use of Protamex at 0.2-0.4% dosage following the use of either 0.75 or 1.5% Alcalase does not improve the protein recovery yield. The protein recovery yield changed from 59.8% at 0% Protamex and 8 hours of hydrolysis time to 57.2-61.0%. However it did help to reduce the ratio of hydrolyzed proteins in the range of above 0.6 kDa and increased the ratio of dimer.

The purity of the hydrolyzed protein extracts as represented by their protein content was found to be similar for Alcalase at various dosages and hydrolysis times as well as for various enzyme combinations and falls within the range of 70-77% (Table 32). The combination of 1.5% Alcalase and 0.2-0.4% Protamex results in slightly lower purity. However the purity can be improved to >80% by subsequent use of UF.

The effect of enzymes and enzyme combinations on the molecular weight distribution of the hydrolyzed protein extract are shown in Table 33. Because hydrolysed proteins in the form of peptides and amino acids have molecular weights mostly below 5 kDa they pass through a 10 KDa membrane that is used to concurrently remove oil and produce a clear extract. Hydrolyzed proteins mainly exist as dimers and monomers.

While Flavourzyme does not improve protein recovery yield significantly, it reduces the ratio of molecular weight in the 0.6-3 kDa range and increases the ratio of monomer and free tryptophan over use of Alcalase alone. Flavourzyme as a $2^{nd}$ enzyme, helps reduce the ratio of hydrolyzed proteins in the range above 0.6 kDa, increased the ratio of dimer at a low dosage of 0.2% and elevates the level of free tryptophan. On the other hand, higher dosage of Flavourzyme increases the ratio of monomer Neutrase also reduces the ratio of molecular weight in the 0.6-3 kDa range and increases the ratio of dimer. Neutrase as a $2^{nd}$ enzyme increased the protein recovery yield, but did not improve the purity of the hydrolyzed protein extract. This enzyme does not release tryptophan.

Based on the results of protein recovery yield, purity of the hydrolyzed protein extract and the molecular weight distribution of hydrolyzed proteins, enzyme combinations of 1.5% Alcalase and 0.2% Flavourzyme and 1.5% Alcalase and 0.2% Neutrase would appear to be preferred combinations.

TABLE 33

The Effect of Enzyme Dosage and Combination
on the Molecular Weight Distribution of Hydrolyzed Protein Extracts.

| Enzyme Combination | Enzyme 1 | Enzyme 2 | Molecular Weight (kDa) | | | | | | Tryptophane (g * 100 g−1) |
|---|---|---|---|---|---|---|---|---|---|
| | | | >10 | 10-5 | 3-5 | 0.6-3 | Dimer | Monomer | |
| 0.75% Alcalase 0.2% Flavourzyme | 0.75% Alcalase | 0.2% Flavourzyme | <1 | 0 | 2 | 18 | 42 | 33 | 0.27 |
| 0.75% Alcalase 0.4% Flavourzyme | 0.75% Alcalase | 0.4% Flavourzyme | <1 | 0 | 2 | 12 | 43 | 38 | 0.39 |
| 0.75% Alcalase 0.75% Flavourzyme | 0.75% Alcalase | 0.75% Flavourzyme | <1 | 0 | 2 | 17 | 37 | 38 | 0.47 |
| 0.75% Alcalase 0.2% Neutrase | 0.75% Alcalase | 0.2% Neutrase | <1 | 0 | 2 | 14 | 47 | 33 | <0.1 |
| 0.75% Alcalase 0.4% Neutrase | 0.75% Alcalase | 0.4% Neutrase | <1 | 0 | 2 | 14 | 51 | 31 | <0.1 |
| 0.75% Alcalase 0.2% Protamex | 0.75% Alcalase | 0.2% Protamex | <1 | 0 | 2 | 15 | 51 | 31 | <0.1 |
| 0.75% Alcalase 0.4% Protamex | 0.75% Alcalase | 0.4% Protamex | <1 | 0 | 2 | 13 | 51 | 31 | <0.1 |
| 0.75% Alcalase 0.75% Alcalase | 0.75% Alcalase | 0.75% Alcalase | 2 | 0 | 2 | 14 | 46 | 33 | <0.1 |

TABLE 33-continued

The Effect of Enzyme Dosage and Combination
on the Molecular Weight Distribution of Hydrolyzed Protein Extracts.

| Enzyme Combination | Enzyme 1 | Enzyme 2 | Molecular Weight (kDa) | | | | | | Tryptophane (g * 100 g-1) |
|---|---|---|---|---|---|---|---|---|---|
| | | | >10 | 10-5 | 3-5 | 0.6-3 | Dimer | Monomer | |
| 1.5% Alcalase 0.2% Flavourzyme | 1.5% Alcalase | 0.2% Flavourzyme | 1 | 0 | 2 | 11 | 54 | 29 | 0.27 |
| 1.5% Alcalase 0.4% Flavourzyme | 1.5% Alcalase | 0.4% Flavourzyme | 1 | 0 | 2 | 10 | 45 | 39 | 0.39 |
| 1.5% Alcalase 0.75% Flavourzyme | 1.5% Alcalase | 0.75% Flavourzyme | 1 | 0 | 2 | 8 | 42 | 44 | 0.49 |
| 1.5% Alcalase 1.5% Flavourzyme | 1.5% Alcalase | 1.5% Flavourzyme | 1 | 0 | 2 | 6 | 40 | 55 | 0.6 |
| 1.5% Alcalase 0.2% Neutrase | 1.5% Alcalase | 0.2% Neutrase | <1 | 0 | 2 | 11 | 48 | 34 | <0.1 |
| 1.5% Alcalase 0.4% Neutrase | 1.5% Alcalase | 0.4% Neutrase | <1 | 0 | 2 | 11 | 48 | 34 | <0.1 |
| 0.75% Alcalase/2 h | 0.75% Alcalase | 2 hours | 1 | 0 | 4 | 20 | 44 | 28 | <0.1 |
| 0.75% Alcalase/3 h | 0.75% Alcalase | 3 hours | 1 | 0 | 4 | 20 | 44 | 28 | <0.1 |
| 0.75% Alcalase/4 h | 0.75% Alcalase | 4 hours | <1 | 0 | 4 | 20 | 44 | 30 | <0.1 |
| 0.75% Alcalase/8 h | 0.75% Alcalase | 8 hours | <1 | 0 | 3 | 18 | 45 | 31 | <0.1 |
| 1.5% Alcalase/2 h | 1.5% Alcalase | 2 hours | 1 | 0 | 4 | 20 | 44 | 28 | <0.1 |
| 1.5% Alcalase/3 h | 1.5% Alcalase | 3 hours | <1 | 0 | 3 | 18 | 44 | 33 | <0.1 |
| 1.5% Alcalase/4 h | 1.5% Alcalase | 4 hours | <1 | 0 | 3 | 19 | 45 | 39 | <0.1 |
| 1.5% Alcalase/8 h | 1.5% Alcalase | 8 hours | <1 | 0 | 3 | 18 | 48 | 28 | <0.1 |
| 1.5% Alcalase 0.2% Protamex | 1.5% Alcalase | 0.2% Protamex | <1 | 0 | 2 | 14 | 48 | 35 | <0.1 |
| 1.5% Alcalase 0.4% Protamex | 1.5% Alcalase | 0.4% Protamex | <1 | 0 | 2 | 14 | 48 | 35 | <0.1 |

EXAMPLE 13

Evaluation of Ultrafiltration to Remove Oil

This example demonstrates the utility of ultrafiltration (UF) to remove the oil present in the hydrolysis process stream where the feed material is cold-crushed meal containing 9-14% oil.

Oily meal was mixed with water in a ratio of 1:7 to form a slurry, the pH of the slurry was adjusted to 7 with sodium hydroxide and then centrifuged at 4000 rpm for 10 minutes to separate the insoluble solids from the aqueous phase. The insoluble solids were collected and washed again at the same 1:7 ratio two more times.

The wet insoluble solids were then mixed with water to provide a slurry containing 10% solids, the slurry was heated to 60° C. and the pH adjusted to 8.3. Alcalase was then added to the slurry at 1% dosage based on the dry weight of starting material. The slurry was allowed to digest with stirring for 4 hours. After 4 hours the temperature was reduced to 50° C. and Flavourzyme was added at a 1% dosage based on dry weight of the starting material. The slurry was digested another 4 hours with stirring.

The hydrolyzed slurry, which had a pH of 6.85, was heated to 30° C. and divided into 2 fractions; one was adjusted to pH 7 with sodium hydroxide and the other was adjusted to pH 4 with hydrochloric acid to determine whether pH modification would cause a change in the quantity of fatty material passing through the membranes by altering the ionization state of the saponified material. The pH 7 slurry was centrifuged at 4000 rpm for 10 minutes to separate the solids fraction from the liquid fraction. The solids were washed with 2 times the volume in water. The liquid from the first separation were combined with the wash from the second separation. The same process was followed for the pH 4 slurry.

The liquids from the pH 7 extract were filtered through a Millipore UF (10 k Dalton MW membrane) and the permeate and retentate fractions were collected and oven dried for further oil analysis. Ultrafiltration was repeated with the extract from the pH 4 procedure in the same manner as described above.

The liquid samples were dried in the oven at 90° C. overnight and were tested for oil content to determine the effectiveness of UF at oil removal.

TABLE 34

| Sample | Oil % (dwb) |
|---|---|
| Washed oily meal, pre-hydrolysis [worst-case testing] | 13 |
| Meal post-hydrolysis [worst-case testing] | 17 |
| Supernatant (UF feed) [worst-case testing] | 1 |
| UF Permeate (Feed pH 7) | 0.0 |
| UF Permeate (Feed pH 4) | 0.12 |

Only a fraction of the oil present is liberated from the oily meal during hydrolysis. Therefore, only a small amount of oil was delivered to the UF for removal (<2%). Table 34 shows the oil content in the permeate to be 0-0.12% oil (dwb) following ultrafiltration. The UF process is therefore capable of removing the small amounts of oily matter liberated into the process stream and to deliver very low levels of oil. When compared with the results of the hydrolysis process performed on defatted meal, levels of oil in the final product are equivalent.

Based on the data obtained from this evaluation, the UF membrane (10 k Dalton MW) was found to be effective in removing oil from the hydrolyzed extract independent of pH of the feed material. The potentially saponified oil was retained by the UF membrane.

Hydrolysed protein previously developed can have a strong flavour with a high bitterness and dark colour. These properties can result in limited applications. Accordingly, selection of an enzyme system or additional unit operation which can modify the taste and colour to be more appropriate for high usage applications, such as sports nutrition, would be advantageous in light of the results obtained in the laboratory evaluations set forth in Examples 11-13 above a larger, pilot scale process for preparing a preferred hydrolyzed concentrate, as described below, was conducted.

EXAMPLE 14

Pilot Production of Hydrolyzed Concentrate

Five batches, as described below, were prepared. One batch was divided into 2 sub batches. The feed material was a partially defatted *B. napus* or *B. juncea* canola meal following cold pressing and had an oil content of ≥2%.

1) *B. juncea* was treated with Alcalase (0.5%)/Flavourzyme (0.13-0.14%).
2) *B. juncea* was treated with Alcalase (1.5%)/Flavourzyme (0.4%).
3) A larger batch (70% larger) than batches 1 or 2 of *B. juncea* feed material was treated with Alcalase (1.5%)/Neutrase (0.2%) and then divided into two sub-batches after ultrafiltration
   a. Sub-batch a) was processed by nanofiltration after ultrafiltration
   b. Sub-batch b) was treated with carbon treatment after ultrafiltration and then subjected to nanofiltration.
4) *B. napus*: overheated prior to Ultrafiltration was treated with Alcalase (1.5%)/Neutrase (0.2%) and then subjected to Carbon Treatment before ultrafiltration.
5) *B. napus* was treated with Alcalase (1.5%)/Neutrase (0.2%).

Pre-Extraction of *Napus* and *Juncea* Material:

*B. napus* was provided as a dry, partially defatted pressed cake meal *B. Juncea* was provided as a wet meal following separation of soluble proteins for the preparation of the isolate by the process described above (See FIG. 4A-4B). pH was adjusted to 5±0.2 (using citric acid for pH adjustment) before the introduction of phytase. Phytase was added at 1.2% based on dry solids. The phytase treated meal was then washed and centrifuged twice resulting in a wet meal with approximately 20-22% solids, the balance being water and oil. The wet meal was then mixed with RO water to provide a slurry of ~8% solids. The slurry was then adjusted to 60° C.±2° C. and pH 8.3±0.2.

Alcalase was added at a rate of 0.5% (batch 1) and 1.5% (batches 2-5) of the dry weight of solids. For example, for a solids content of 200 kg, 3 kg of Alcalase was added in batch 2. The enzyme was stirred with the meal for 4 hours. Following the Alcalase treatment, the slurry was cooled to 50±2° C.

For batches 1 & 2, Flavourzyme was added at 0.13% (batch 1) or 0.4% (batch 2) of the dry weight of solids (same dry weight used for Alcalase addition). For example, for batch 2, 0.8 kg of Flavourzyme was added for 200 kg dry solids. The Flavourzyme treatment was for an additional 4 hours. For batches 3, 4, & 5, 0.2%, Neutrase was added based on the same dry weight of solids and then held for 4 hours.

Hydrolysate Recovery:

Following the enzyme treatment the treated slurry was centrifuged using a Westfalia Decanter Centrifuge and a disk-stack centrifuge to separate the hydrolyzed protein extract from the insoluble solids. The extract had insoluble solids of <0.1% v/v. The solids were further washed by mixing them with RO water at a ratio of 1 to 2 by weight and centrifuged again to separate any additional soluble hydrolyzed protein from the washed solids. Centrifuge Separation at 1100-1400 L/hr gave settleable solids of 0.1%

The extract from the two product recovery decantings (referred to as desludged extract) were collected and adjusted to pH 7 using citric acid. The temperature of the slurry and extracts was maintained at 55-60° C. throughout. The extract was then pasteurized at a temperature of 72-74° C. for about 20 seconds.

Ultrafiltration:

To allow only small molecular weight material to be recovered and exclude high molecular weight and oily materials the desludged extract was subject to ultrafiltration. While the starting solution (desludged extract) was murky and opaque, the ultrafiltration permeate was coloured but transparent. Ultrafiltration (UF) parameters were: inlet pressure 55-60 pis, outlet pressure 10-15 psi, temperature 55-60° C., 10,000 MWCO membranes.

The material was ultrafiltered down to 90-95% of the original volume and the permeate collected. Once the volume was reduced, an equal amount of RO water was added and permeated to the original concentrated level (Diafilter (DF)). The procedure was repeated again. and DF permeates were combined.

Carbon Treatment

Batch 3 was split into two portions. Portion a) was exposed to nanofiltration while portion b) was adjusted to pH 6 and then mixed with carbon and a filter aid. The solids were then removed using a plate and frame filter press dressed with filter aid. The added carbon was 25% of the solids content in the solution. The carbon containing solution was mixed for 30 minutes before addition the filter aid at 50% of the solids content.

In Batch 4, the solution was subjected to carbon treatment after it was found to have been over heated to 92° C. prior to ultrafiltration. This used contact ratios of 25% carbon and 100% filter aid based on the incoming solids.

Nanofiltration

The permeate from the ultrafiltration stage was subjected to nanofiltration to remove excess water and salts and the increase the solids concentration prior to spray drying. Nanofiltration (UF) parameters were an Inlet pressure of 250 psi (the outlet pressure was 220-232 psi) at a temperature of 30° C. The NF retentate (the hydrolyzed protein extract) was pasteurized at a temperature of 72-74° C. for about 20 seconds.

Spray Drying

The concentrated hydrolyzed protein extract following nanofiltration (at ambient temperature) was then fed to a spray dryer having an inlet air temperature of 170±5° C. The outlet air temperature was adjusted to 80±5° C. to obtain a spray dried product with a moisture content of 6±1%.

Results and Discussion

General Results of Hydrolysate Production:

Comparison of various properties of the products produced in the five above referenced runs is shown in Tables 35 and 36.

TABLE 35

Analysis of Products from Hydrolysis Treatment

| | Trial No: | | | | |
|---|---|---|---|---|---|
| | 1 | 2 | 3a | 3b | 5 |
| Seed Type | Juncea | Juncea | Juncea | Juncea | Napus |
| Physico-Chemical Analysis | | | | | |
| Protein (Nx 6.25) 'as is' | 91.6% | 85.5% | 87.5% | 88.8% | 76.9% |
| Protein (Nx 6.25) 'dwb' | 94.6% | 89.4% | 90.3% | 91.9% | 79.2% |
| Moisture & Volatiles (% as is) | 3.18 | 4.39 | 3.06 | 3.39 | 2.87 |
| Solubility (as % of CP) | 99.9 | 99.9 | 99.9 | 99.9 | 99.9 |

TABLE 35-continued

Analysis of Products from Hydrolysis Treatment

| | Trial No: | | | | |
|---|---|---|---|---|---|
| | 1 | 2 | 3a | 3b | 5 |
| Solubility (% Soluble Crude Protein as is) | 91.5 | 85.4 | 87.4 | 88.7 | 76.8 |
| Carbohydrate (% dwb by difference) | −0.04 | 3.58 | 0.41 | 3.88 | 7.09 |
| Fat (% dwb swedish tube) | 0.4 | 0.0 | 0.0 | 0.0 | 0.2 |
| Fat (% dwb by acid hydrolysis) | 0.24 | 0.34 | 0.24 | 0.19 | 0.32 |
| Ash (%) | 4.8 | 6.5 | 9.0 | 3.9 | 12.9 |
| Fiber (% AOCS Ba 6-84) | 0.06 | 0.03 | 0.03 | 0.03 | 0.04 |
| Total Glucosinolates (μmol/g) | 0.06 | <DL | 0.06 | 0.05 | 0.06 |
| Total Phytates (% Phytic Acid) | 0.42 | 0.46 | 0.50 | 0.50 | 0.98 |
| Total minerals (g/100 g) | 3.34 | 3.16 | 4.23 | 3.63 | 5.59 |

Ultrafiltration was found to be very effective in excluding the oil carried over from the initial meal from being incorporated in the final product. This unit operation also assured that the hydrolyzed protein in final product was completely soluble.

TABLE 36

Organoleptic and Yield of Hydrolysis Products

| | Trial No: | | | | |
|---|---|---|---|---|---|
| | 1 | 2 | 3a | 3b | 5 |
| Seed Type | Juncea | Juncea | Juncea | Juncea | Napus |
| Organoleptic Analysis | | | | | |
| Visual inspection | Tan | Yellowish tan | Tan | Off white | Yellow |
| Flavour | Medium bitter moderate brothy | Stronger bitter & brothy | Less bitter more like old cheddar | Milder than 3a | Stronger bitter flavor |
| Dry Powder Colour (Hunter L) | 78.67 | 75.04 | 79.06 | 84.96 | 76.52 |
| Colour in 1% solution (Hunter L) | 67.63 | 66.15 | 68.58 | 76.41 | 60.57 |
| Colour in 5% solution (Hunter L) | 36.93 | 31.61 | 41.13 | 62.73 | 25.95 |
| Yield of product | | | | | |
| Protein in washed meal (kg/1000 kg initial wet meal) | 57 | 60 | 56.5 | 56.5 | 32.4 |
| Protein Extracted (kg/1000 kg initial wet meal) | 34 | 33.5 | 40.3 | 40.3 | 17 |
| Extraction efficiency by hydrolysis (% of total protein) | 53% ± 5% | 56% ± 5% | 67% ± 5% | 67% ± 5% | 50% ± 5% |
| dry solids through Ultrafiltration/1000 kg wet meal | 35.5 | 31.1 | 39.1 | 35.6 | 19.5 |
| Ultrafiltration Protein passage [based on 100% extract passage] | 100% | 73% ± 8% | 88% | 88% | 90% |
| Mechanical Yield (Nanofiltration and spray drying) | 67% | 78% | 79% | 79% | 76% |

Extraction with Flavourzyme was highly effective for both the low dose and high dose systems with 53% and 57% protein extraction respectively. Neutrase resulted in higher extraction at 67% of the total meal protein. When using the meal from the *napus* seed, the low residual protein translated to a lower available protein as well as a lower relative efficiency of enzymatic extraction of only 50%, presumably due to high amounts of high molecular weight materials.

Ultrafiltration of the low dosage Flavourzyme system (0.14%) resulted in 100% of the proteins being recovered. Higher levels of hydrolysis led to lower recoveries of approximately 90% for the Neutrase system and approx. 73%±8% for the high dose (0.4%) Flavourzyme system.

The low enzyme dosage alcalase/flavourzyme system (Batch 1) resulted in excellent protein purity with equivalent solubility. As shown in Table 34, the flavor was quite good. The lower enzyme use provides a lower degree of hydrolysis and as such can have a potentially stronger immunogenic response. Low dose Flavourzyme of batch 1 resulted in the best overall recovery and protein purity. The low enzyme system also improved the colour of the product both as a dry powder and a solution.

Use of the Neutrase enzyme system resulted in a lighter product both dry and in solution and when coupled with carbon treatment the product was further improved. The carbon treated Neutrase product was a light off white colour and when prepared as a 5% solution was a light straw colour compared to the dark tea colour resulting from the other hydrolysates. Further results from the carbon treatment are discussed in regard to FIGS. 5 and 6, and Table 37-39 below. The *Napus* derived hydrolysate was substantially darker than the other runs, both dry and wet, as shown by the low hunter L numbers above, and was decidedly more yellow.

The protein products had reasonable minerals levels for hydrolyzed protein with sodium levels of 1.5%-2.5% for all *juncea* lots and acceptable calcium levels. As shown in Table 37, there is strong correlation between total mineral content, especially sodium, and phytate levels. The use of the carbon treatment led to increases in chloride (the acid used to decrease pH was food-grade HCl) and phosphorous as well as aluminum and cadmium. This is probably due to metals in the filter aid material. The sulphur content was due to the high level of sulphur containing amino acids in the protein.

TABLE 37

Mineral Content of Each Hydrolyzed product

| | Trial No: | | | | |
|---|---|---|---|---|---|
| | 1 | 2 | 3a | 3b | 5 |
| Seed Type | Juncea | Juncea | Juncea | Juncea | Napus |
| | Minerals ***SRC reports ug/g | | | | |
| Chloride (water soluble) | <120 | <120 | <50 | 2060 | 370 |
| Aluminum | <0.5 | <0.5 | <0.5 | 2.9 | <0.5 |
| Arsenic | <0.05 | <0.05 | <0.05 | 0.12 | <0.05 |
| Cadmium | 0.03 | 0.02 | 0.02 | 0.05 | 0.02 |
| Calcium | 1220 | 420 | 560 | 730 | 440 |
| Chromium | <0.5 | <0.5 | 0.7 | 3.2 | <0.5 |
| Cobalt | 0.04 | 0.06 | 0.06 | 0.08 | 0.03 |
| Copper | 17 | 11 | 22 | 13 | 4.0 |
| Iodine | <0.5 | <0.5 | <0.5 | <0.5 | <0.5 |
| Iron | 11 | 13 | 14 | 40 | 8.3 |
| Lead | 0.02 | <0.01 | 0.03 | 0.05 | <0.01 |
| Magnesium | 1220 | 690 | 650 | 740 | 1100 |
| Manganese | 2.7 | 1.3 | 1.4 | 3.1 | 2.7 |
| Molybdenum | 1.1 | 1.9 | 2.2 | 4.4 | 0.9 |
| Mercury | <0.005 | <0.005 | <0.005 | <0.005 | <0.005 |
| Phosphorous | 2120 | 1550 | 1760 | 4630 | 3330 |
| Potassium | 2130 | 1730 | 1440 | 880 | 5690 |
| Selenium | 4.8 | 5.5 | 5.1 | 5.2 | 5.4 |
| Sodium | 14600 | 15400 | 25200 | 14800 | 32500 |
| Sulfur | 12100 | 11800 | 12600 | 12400 | 12400 |
| Zinc | 16 | 22 | 12 | 5.5 | 9.1 |
| Total Minerals g/100 g | 3.34% | 3.16% | 4.23% | 3.63% | 5.59% |

TABLE 37-continued

Mineral Content of Each Hydrolyzed product

| | Trial No: | | | | |
|---|---|---|---|---|---|
| | 1 | 2 | 3a | 3b | 5 |
| Total Heavy Metals (As, Pb, Hg, Cd) ug/g | 0.105 | 0.085 | 0.105 | 0.225 | 0.04 |

One of the primary purposes for development of the hydrolyzed protein is to recover maximum value from the seed by producing soluble proteins (or peptides) suitable for nutritional purposes. Each of the above described batches resulted in highly nutritious protein profiles with amino acid scores of ~1.24 for the Flavourzyme systems and 1.13-1.18 for the Neutrase system.

TABLE 38

Hydrolysates Amino Acid Profile

| | Trial No: | | | | |
|---|---|---|---|---|---|
| | 1 | 2 | 3a | 3b | 5 |
| Seed Type | Juncea | Juncea | Juncea | Juncea | Napus |
| | Amino acid profile (g/100 g product as is) | | | | |
| Aspartic acid | 7.32 | 6.29 | 6.42 | 6.67 | 6.09 |
| Glutamic acid | 18.1 | 17.1 | 18.2 | 20 | 15.9 |
| Serine | 3.91 | 2.48 | 4.55 | 4.84 | 4.3 |
| Glycine | 4.71 | 4.46 | 4.64 | 4.86 | 4.09 |
| Histidine | 3.45 | 3.63 | 3.5 | 3.47 | 2.55 |
| Arginine | 5.10 | 2.14 | 5.1 | 4.63 | 3.49 |
| Threonine | 3.60 | 3.15 | 3.62 | 3.74 | 3.36 |
| Alanine | 3.99 | 3.86 | 4.08 | 4.49 | 3.71 |
| Proline | 5.52 | 5.52 | 5.5 | 5.29 | 5.43 |
| Tyrosine | 3.16 | 2.20 | 2.96 | 2.78 | 2.97 |
| Valine | 4.87 | 5.01 | 4.27 | 4.51 | 4.22 |
| Methionine | 2.06 | 2.03 | 2.12 | 2.32 | 2.03 |
| Cystine | 2.12 | 2.17 | 2.29 | 2.21 | 2.16 |
| Isoleucine | 4.12 | 4.30 | 3.62 | 3.74 | 3.13 |
| Leucine | 7.07 | 7.09 | 6.82 | 7.27 | 5.96 |
| Phenylalanine | 3.98 | 4.07 | 3.75 | 3.72 | 3.43 |
| Lysine | 5.31 | 4.92 | 4.76 | 5.05 | 4.42 |
| Tryptophan | 1.37 | 1.47 | 1.39 | 0.96 | 1.08 |
| Total Amino Acids | 89.7 | 81.9 | 87.6 | 90.6 | 78.3 |
| Non amino acid material | 10.3 | 18.1 | 12.4 | 9.4 | 21.7 |
| Amino Acid Score | 1.233 | 1.252 | 1.132 | 1.161 | 1.176 |

TABLE 39

Amino Acid Quality Profile

| | WHO FAO recommended pattern for 3-10 yr olds† | Trial No: | | | | |
|---|---|---|---|---|---|---|
| | | 1 | 2 | 3a | 3b | 5 |
| | | Seed Type | | | | |
| | | Juncea | Juncea | Juncea | Juncea | Napus |
| | Amino acid profile (g/100 g protein) | | | | | |
| Aspartic acid | | 8.2% | 7.7% | 7.3% | 7.4% | 7.8% |
| Glutamic acid | | 20.2% | 20.9% | 20.8% | 22.1% | 20.3% |
| Serine | | 4.4% | 3.0% | 5.2% | 5.3% | 5.5% |
| Glycine | | 5.3% | 5.4% | 5.3% | 5.4% | 5.2% |
| Histidine | 1.6% | 3.8% | 4.4% | 4.0% | 3.8% | 3.3% |

TABLE 39-continued

Amino Acid Quality Profile

| | WHO FAO recommended pattern for 3-10 yr olds† | Trial No: 1 Juncea | 2 Juncea | 3a Seed Type Juncea | 3b Juncea | 5 Napus |
|---|---|---|---|---|---|---|
| Arginine | | 5.7% | 2.6% | 5.8% | 5.1% | 4.5% |
| Threonine | 2.5% | 4.0% | 3.8% | 4.1% | 4.1% | 4.3% |
| Alanine | | 4.4% | 4.7% | 4.7% | 5.0% | 4.7% |
| Proline | | 6.2% | 6.7% | 6.3% | 5.8% | 6.9% |
| Tyrosine | (4.1%*) | 3.5% | 2.7% | 3.4% | 3.1% | 3.8% |
| Valine | 4% | 5.4% | 6.1% | 4.9% | 5.0% | 5.4% |
| Methionine | 1.2% | 2.3% | 2.5% | 2.4% | 2.6% | 2.6% |
| Cystine | 1.2% | 2.4% | 2.6% | 2.6% | 2.4% | 2.8% |
| Isoleucine | 3.1% | 4.6% | 5.3% | 4.1% | 4.1% | 4.0% |
| Leucine | 6.1% | 7.9% | 8.7% | 7.8% | 8.0% | 7.6% |
| Phenylalanine | (4.1%*) | 4.4% | 5.0% | 4.3% | 4.1% | 4.4% |
| Lysine | 4.8% | 5.9% | 6.0% | 5.4% | 5.6% | 5.6% |
| Tryptophan | 0.66% | 1.5% | 1.8% | 1.6% | 1.1% | 1.4% |
| Total Amino Acids | | 100.0% | 100.0% | 100.0% | 100.0% | 100.0% |
| Ratio of Non-amino acid material/amino acids | | 11.5% | 22.1% | 14.2% | 10.4% | 27.7% |

*Combined aromatic amino acid recommendation 4.1 g/100 g protein
†WHO FAO Recommended protein pattern for 3-10 yr olds 2007 (WHO technical report series 935)

Figure 5:
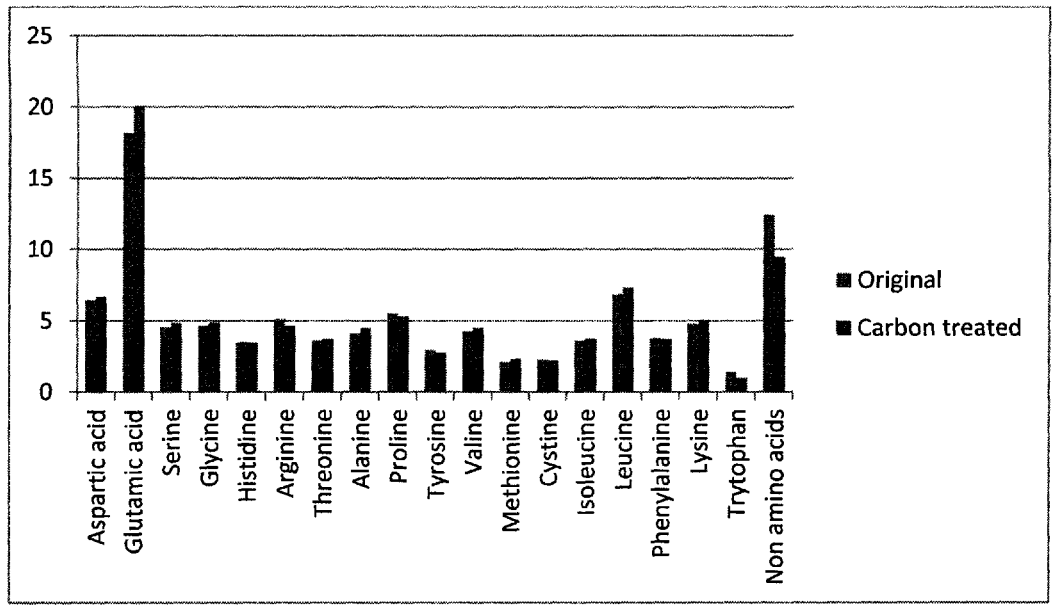
FIG. 5 is a graph comparing the amino acid profile of a hydrolyzed protein with and without carbon treatment.
Figure 6:
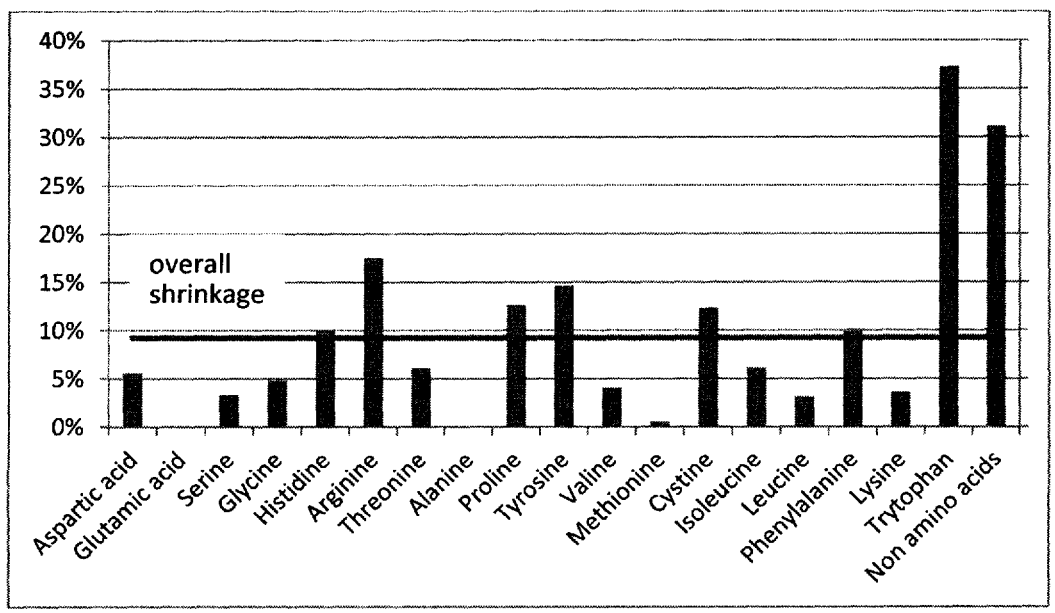
FIG. 6 is a graph illustrating shrinkage of amino acids and non amino acid material through carbon treatment, shown as Δ% of Initial content of each Amino Acid.

Total tryptophan was reduced with carbon treatment when Neutrase was the secondary enzyme. This is due to the retention of tryptophan in dimer and larger molecules when using Neutrase. In contrast, Flavourzyme was found in the past to liberate tryptophan as a free amino acid which would subsequently be absorbed during carbon treatment. Carbon treatment also resulted in absorption of non-amino acid/peptide materials and an improvement in purity. This is also evidenced by the significant removal of colour which results in a protein solution with a pale straw colour as opposed to the light brown seen in the product not subjected to carbon treatment As shown in FIG. 5, the amino acid profile had no significant change as a result of the carbon treatment but there was some change as a result of specific absorption of peptide and amino acids on the carbon. The resulting protein product was still well balanced with a good amino acid score. In fact, the carbon treatment improved the overall amino acid score compared to the untreated batch.

By assuming that no amino acid can be transformed or generated by the carbon treatment, it is possible to estimate the minimum degree of shrinkage due to carbon treatment even if it is not apparent from the yield of finished product. The amino acid with the highest relative increase in proportion was alanine and thus assuming that it was 100% retained, we see in Table 40 and FIG. 6 that the total product mass shrank by 9.2%. The greatest absolute change were for arginine and non-amino acid material at 0.9 g/100 g and 3.9 g/100 g loss while the highest relative loss was with the non-amino acid material and tryptophan at 31.1% and 37% respectively. These changes served to improve the balance in the protein quality and further purify the protein. The loss of tryptophan was acceptable when compared with the required value.

TABLE 40

Shrinkage Of Amino Acids And Non Amino Acid Material Through Carbon Treatment

| Batch 3 | Before carbon [g/100 g starting] | After carbon [g/100 g starting] | Loss to carbon [g/100 g starting] | Relative loss |
|---|---|---|---|---|
| Aspartic acid | 6.42 | 6.06 | 0.359 | 5.6% |
| Glutamic acid | 18.2 | 18.17 | 0.026 | 0.1% |
| Serine | 4.55 | 4.40 | 0.152 | 3.3% |
| Glycine | 4.64 | 4.42 | 0.224 | 4.8% |
| Histidine | 3.5 | 3.15 | 0.347 | 9.9% |
| Arginine | 5.1 | 4.21 | 0.893 | 17.5% |
| Threonine | 3.62 | 3.40 | 0.222 | 6.1% |
| Alanine | 4.08 | 4.08 | 0.000 | 0.0% |
| Proline | 5.5 | 4.81 | 0.693 | 12.6% |
| Tyrosine | 2.96 | 2.53 | 0.434 | 14.7% |
| Valine | 4.27 | 4.10 | 0.172 | 4.0% |
| Methionine | 2.12 | 2.11 | 0.012 | 0.6% |
| Cystine | 2.29 | 2.01 | 0.282 | 12.3% |
| Isoleucine | 3.62 | 3.40 | 0.222 | 6.1% |
| Leucine | 6.82 | 6.61 | 0.214 | 3.1% |
| Phenylalanine | 3.75 | 3.38 | 0.370 | 9.9% |
| Lysine | 4.76 | 4.59 | 0.171 | 3.6% |
| Tryptophan | 1.39 | 0.87 | 0.518 | 37.2% |
| Total Non-Amino acid | 12.4 | 8.54 | 3.858 | 31.1% |
| Total product (as is) | 100 | 90.82 | 9.167 | 9.2% |

Effect on Molecular Weight Distribution

A comparison of the enzyme systems, see Table 41, shows that the Neutrase system produced lower levels of mono amino acids and did not produce any free tryptophan in solution while the low enzyme dose alcalase/flavourzyme system in Batch 1 resulted in substantially less monomeric amino acid than the higher dosage used in Batch 2 and approx. 35% lower free tryptophan. The Neutrase system was more effective at breaking down the proteins to molecular weights below 600 Daltons in the *juncea* runs. As the body has different transport mechanisms for short dimer and trimer peptides than for free amino acids because the liver rapidly depletes free amino acids in the blood stream, there is great advantage to limiting the degree of hydrolysis to maximize retention of short peptides. The low free tryptophan limited the negative effect of carbon treatment on the amino acid profile whereas lab studies using the Flavourzyme system resulted in as much as 95% of the tryptophan being lost when Flavourzyme was used at a high dosage (ca. 1.5% of dry solids).

One of the key aspects of the production of hydrolysed proteins is that the partial enzymatic digestion of the proteins lowers the immunogenic response to the protein. This is highly importance in specialized applications such as medical and pediatric nutrition where the recipient has either a compromised or immature immune system and may have limited ability to communicate. Previously, various test samples of hydrolyzed protein have been targeted to these markets. The

TABLE 41

Effect of treatment on Molecular Weight Profile:

| | | Batch # | | | | |
|---|---|---|---|---|---|---|
| | | 1 | 2 | 3a | 3b | 5 |
| Source | | Juncea | Juncea | Juncea | Juncea | Napus |
| Enzyme Combination | | Alcalase/ Flavourzyme | Alcalase/ Flavourzyme | Alcalase/ Neutrase | Alcalase/ Neutrase | Alcalase/ Neutrase |
| Enzyme 1 Alcalase | | 0.5% | 1.5% | 1.5% | 1.5% | 1.5% |
| Enzyme 2 | | 0.14% | 0.4% | 0.2% | 0.2% | 0.2% |
| | | Flavourzyme | Flavourzyme | Neutrase | Neutrase | Neutrase |
| Carbon Treatment | | | | | 2.5% of solution | |
| Molecular | >10 | 0 | 0 | 0 | 0 | 0 |
| Mass (kDa) | 10-5 | 0 | 0 | 0 | 0 | 0 |
| | 3-5 | 0 | 0 | 0 | 0 | 3 |
| | 0.6-3 | 25 | 16 | 9 | 9 | 10 |
| | Dimer | 37 | 35 | 62 | 63 | 53 |
| | Monomer | 36 | 47 | 28 | 26 | 32 |
| Free Tryptophan (g * 100 g$^{-1}$) | | 0.27 | 0.42 | <0.1 | <0.1 | <0.1 |

Hydrolysis of washed *napus* meal resulted in the presence of high molecular weight material, with 3% of the proteins being in the 3-5 kDa range. This indicates a lower degree of hydrolysis or less hold up by the ultrafiltration membrane when compared to earlier tests on *B. juncea* run without nanofiltration and ultrafilteration. (See Table 42) The membrane processing eliminates the over 3 kDa material and substantially changes the peptide size profile for both the Alcalase/Flavourzyme system and the Alcalase/Neutrase systems. For the Neutrase system, the molecular weight distribution is greatly skewed toward the dimer while the mono amino acid content is lessened and the high molecular weight material is reduced.

best received prior sample was the product produced by treating washed defatted canola meal generated from the previous solvent based process and subsequently hydrolyzed for 4 hours with 1% Alcalase and 1% Flavourzyme. Several samples were also prepared using the Protomex as the secondary enzyme or lower enzyme use to effect different degrees of hydrolysis. When the Protomex system was used, the immunogenic response was higher than when using a Flavourzyme system with the same molecular weight distribution and degree of hydrolysis. This suggests that Flavourzyme is more appropriate for lowering of immunogenicity. Lower degrees of hydrolysis also led to higher immunogenic response.

TABLE 42

Change in Molecular Weight Profile from Lab to Pilot Plant

| | | Batch # | | | | | |
|---|---|---|---|---|---|---|---|
| | | LAB DATA | 1 | LAB DATA | 2 | LAB DATA | 3A |
| Source | | Juncea | Juncea | Juncea | Juncea | Juncea | Juncea |
| Enzyme Combination | | Alcalase/ Flavourzyme | Alcalase/ flavourzyme | Alcalase/ Flavourzyme | Alcalase/ flavourzyme | Alcalase Neutrase | Alcalase/ Neutrase |
| Enzyme 1 Alcalase | | 0.75% | 0.5% | 1.5% | 1.5% | 1.5% | 1.5% |
| Enzyme 2 | | 0.2% | 0.14% | 0.4% | 0.4% | 0.2% | 0.2% |
| | | Flavourzyme | Flavourzyme | Flavourzyme | Flavourzyme | Neutrase | Neutrase |
| Carbon Treatment | | | | | | | |
| Molecular | >10 | <1 | 0 | <1 | 0 | 1 | 0 |
| Mass (kDa) | 10-5 | 0 | 0 | 0 | 0 | 0 | 0 |
| | 3-5 | 2 | 0 | 2 | 0 | 2 | 0 |
| | 0.6-3 | 18 | 25 | 10 | 16 | 11 | 9 |
| | Dimer | 42 | 37 | 45 | 35 | 48 | 62 |
| | Monomer | 33 | 36 | 39 | 47 | 34 | 28 |
| Free Tryptophan (g * 100 g$^{-1}$) | | 0.27 | 0.27 | 0.39 | 0.42 | <0.1 | <0.1 |

Table 43 compares the materials prepared above in Example 14 with the results from a prior hydrolysed protein prepared from the washed defatted canola meal. Neutrase was found to be very effective at hydrolyzing the insoluble protein and enabling extraction. The resulting hydrolysate had no free tryptophan and a molecular weight profile superior to the Flavourzyme material in regards to potential immunogenic response.

The molecular weight profile of Batch 2, (Alcalase and Flavourzyme at 1.5% and 0.4% respectively), appears to be a suitable alternative to sample product that was previously shown to and tested by customers. Neutrase appears to achieve a similar molecular profile but this does not mean that it will adequately lower the immunogenicity response due to the specificity of protein hydrolysis patterns when using enzymatic hydrolysis.

Amino Acid Scores of over 1.13 based on the scoring pattern recommended for 3-10 ys old by the World Health Organization. In addition, the use of both ultrafiltration and nanofiltration resulted in high protein purities of over 85% (Nx6.25) on an as is basis compared to ~75% protein purity for previous runs performed using washed defatted *juncea* meal without nanofiltration.

The enzyme processing hydorlyzes approximately 60% of the insoluble protein in the washed meal. This varied by hydrolysis system with the Flavourzyme system resulting in ~55% extraction of protein and the Neutrase system having 67% enzymatic extraction. This is a result of endopeptidase activity of Neutrase leading to greater cleavage of the insoluble protein in contrast to the Flavourzyme which acts on the ends of protein chains. The *Napus* feed material appears to have a lower enzymatic efficiency, probably due to

TABLE 43

Molecular Weights from Hydrolysis of Defatted vs Undefatted Washed Canola

| | Batch # | | | | | |
|---|---|---|---|---|---|---|
| | 0101213-A | 101107D | 20101213-D | 1 | 2 | 3 |
| Source | Defatted Juncea press cake | Defatted Juncea press cake | Defatted Juncea press cake | Undefatted Juncea washed Canola meal | Undefatted Juncea washed Canola meal | Undefatted Juncea washed Canola meal |
| Allergenicity | Low (1.6 titer) | Standard product | Moderate (1.95 titer) | | | |
| Enzyme Combination | Alcalase/ Flavourzyme | Alcalase/ Flavourzyme | Alcalase/ Flavourzyme | Alcalase/ Flavourzyme | Alcalase/ Flavourzyme | Alcalase/ Neutrase |
| Enzyme 1 Alcalase | 1% | 1% | 0.5% | 0.5% | 1.5% | 1.5% |
| Enzyme 2 (Flavourzyme) | 1% | 1% | 0.25% | 0.14% | 0.4% | 0.2% Neutrase |
| Molecular Mass (kDa) >10 | 0 | 0 | 0 | 0 | 0 | 0 |
| 10-5 | 0 | 0 | 1 | 0 | 0 | 0 |
| 3-5 | 0 | 1 | 2 | 0 | 0 | 0 |
| 0.6-3 | 13 | 10 | 20 | 25 | 16 | 9 |
| Dimer | 44 | 43 | 44 | 37 | 35 | 62 |
| Monomer | 42 | 43 | 31 | 36 | 47 | 28 |
| Free Tryptophan (g * 100 g$^{-1}$) | 0.81 | 0.81 | 0.4 | 0.27 | 0.42 | <0.1 |

In regard to proteins and immunogenicity, material having a molecular weight over 3000 Daltons generally has a higher immunogenic response and relative rabbit immunogenicity response after 35 days of exposure to a protein. The protein must be under a log 1.5 titer to qualify as hypoallergenic. All samples from the *juncea* products described in Example 9 meet the first criteria, but have not been tested in animal models.

Alcalase/Flavourzyme is a proven system for lowering the immunogenic response and creates a product with a quantified and improved response. For modeling purposes it is believed that the highest dosing of Alcalase and Flavourzyme (1.5% and 0.4% respectively) may be necessary to bring the product below the 1.5 titer mark defined as hypoallergenic. Neutrase shows great potential for also achieving the requisite low immunogenic response.

Review of the permeation data from the two different enzyme systems shows that the ultrafiltration was faster when using the low enzyme Alcalase/Flavorzyme system of Batch 1. Nanofiltration of the extract successfully concentrated the extract to a more appropriate volume for spray drying.

In summary, the evaluations with the washed *Juncea* canola meal all yielded good quality hydrolyzed proteins with the lower protein concentration in solution and the larger molecular weight of the insoluble proteins in the starting material.

All evaluations using *Juncea* seed resulted in all the molecular weights of the hydrolyzed protein being under 3 kDa, which is the recommended range for hypoallergenic materials. While the cleavage pattern for Neutrase was not tested for reduction in immunogenic response, based on the molecular weight profile of these hydrolyzed materials, they are believed to meet the standard for hypoallergenic materials. Otherwise, the preferred enzyme combination for low allergenicity products, is the 1.5% Alcalase/0.4% Flavourzyme dosing system.

Use of *Napus* meal showed that the higher protein extractability of *Napus* leads to less protein recovery by hydrolysis and consequently higher non-protein material in the hydrolysate. The final *napus* product also had a stronger flavour and a darker more intense colour. However, subsequent extraction runs have confirmed the higher primary stage extractability of the *Napus* material and a molecular weight profile skewed to larger sizes. If the residual proteins in the *Napus* meal are on average larger than those in the *juncea* meal, the average molecular weight after a given period of hydrolysis would be expected to be larger.

Reducing the dosage of Alcalase and Flavourzyme by 66% during hydrolysis from the above preferred level resulted in excellent recovery and excellent protein purity of >90%. While the extent of hydrolysis was lessened, it was still very high with 100% of the protein under 3 kDa and over 75% dimer or mono amino acid. The lower hydrolysis also improved the flavor profile over the more highly hydrolyzed material. Changing the enzyme system to Alcalase and Neutrase resulted in a very high degree of hydrolysis, lower mono amino acids, no free tryptophan and a different, but acceptable, flavour profile.

Carbon treatment was very beneficial in removing the colour from the hydrolysate and improving the flavor profile. While aromatic amino acids were absorbed in the process, the final amino acid profile was improved over the material that was not subjected to carbon treatment when using the Alcalase-Neutrase hydrolysis system. The final amino acid profile was enriched in glutamic acid, which is generally perceived as having a better flavor due to the umami effect. The greatest change in composition was the absorption of non-amino acid materials and subsequently the final purity was over 90% with essentially no non-protein nitrogen.

Ultrafiltration was effective at excluding oil from the end product but requires extensive cleaning of the membranes to maintain flux rate throughout the ultrafiltration process. Nanofiltration was very beneficial at concentrating the protein prior to spray drying and improved the purity of the hydrolyzed protein.

We claim:

1. A process for producing a protein isolate from an oilseed meal, said oil seed meal not having been subjected to extraction with a solvent to remove oil and said oil seed meal being provided by cold pressing at a temperature of 85° C. or less, comprising:
    mixing the oilseed meal with an aqueous solvent comprising water without any added salt to form a slurry;
    if phytic acid is present in the oil seed meal, treating the slurry with phytase at a temperature and a pH suitable for phytase activity;
    separating the slurry with a solid/liquid separation process to form:
        a liquid phase, comprising the aqueous solvent, soluble protein and oil; and
        a slurry solid phase;
    separating the liquid phase to form:
        an oil phase; and
        an aqueous soluble protein phase;
    subjecting the aqueous soluble protein phase to membrane filtration to obtain a protein solution; and
    drying the protein solution to obtain the protein isolate, said protein isolate comprising a mixture of proteins having a range of molecular weights, wherein the protein isolate comprises at least 90% protein (w/w) on a dry weight basis.

2. The process according to claim 1, wherein the process further comprises mixing the solid phase the slurry solid phase with the aqueous solvent comprising water without any added salt and repeating the solid/liquid separation from one to four times.

3. The process according to claim 1, wherein the ratio of the oilseed meal to the aqueous solvent is between 1:6 to 1:15 (w/w) of meal to solvent.

4. The process according to claim 3, wherein the ratio of the oilseed meal to the aqueous solvent is 1:8 to 1:12.5 (w/w) of meal to solvent.

5. The process according to claim 1 including the phytase treatment, wherein the temperature suitable for phytase activity is between 20° and 65° C. and the pH suitable for phytase activity is between 4.5 and 7.5.

6. The process according to claim 5, wherein the temperature suitable for phytase activity is 50° C.-55° C. and the pH suitable for phytase activity is between 5.8-6.2.

7. The process according to claim 1 wherein the solid/liquid separation is conducted by centrifugation.

8. The process according to claim 7, wherein the solid/liquid separation of the mixture is conducted by a decanter centrifuge.

9. The process according to claim 8, wherein the decanter centrifuge is operated at a g-force between 2,000-4,000 g.

10. The process according to claim 9, wherein the g-force is 3,000 g.

11. The process according to claim 7, wherein the centrifugation comprises a decanter centrifuge followed by a first and second disk stack centrifuge in series.

12. The process according to claim 11, wherein the first disk stack centrifuge is operated at a g-force between 6,000-9,000 g, and the second disk stack centrifuge is operated at a g-force between 8,000 g-12,000 g.

13. The process according to claim 12, wherein the first disk stack centrifuge is operated at a g-force of 8,300 g, and the second disk stack centrifuge is operated at a g-force of 10,000 g.

14. The process according to claim 1, wherein the separation of the liquid phase is conducted by centrifugation.

15. The process according to claim 11, wherein the separation of the liquid phase is conducted by a skimming centrifuge, a disk stack centrifuge, a 2-phase centrifuge or a 3-phase centrifuge or a combination thereof.

16. The process according to claim 12, wherein the separation of the liquid phase is conducted by a disk stack centrifuge.

17. The process according to claim 12, wherein the centrifuge is operated at a g-force between 2,000-10,000 g.

18. The process according to claim 14, wherein the centrifuge is operated at a g-force of −6,000 g.

19. The process according to claim 1, wherein the aqueous protein phase is subjected to ultrafiltration followed by diafiltration to obtain a retentate suitable for spray drying comprising the protein solution.

20. The process according to claim 1, wherein the protein isolate comprises less than 2% (w/w) of oil.

21. The process according to claim 1 wherein the oilseed meal comprises species of mustard seed, broccoli seed, flax seed, cotton seed, hemp seed, safflower seed, sesame seed or soybean meal.

22. The process according to claim 21, wherein the species of rapeseed comprises canola.

23. The process according to claim 1 wherein the process is a continuous process.

24. The process according to claim 1 wherein the solid phase is dried and solvent extracted to isolate oil.

25. The process according to claim 1 wherein the slurry is further treated with cellulase.

26. The process according to claim 1 wherein membrane filtration comprises one or more steps of microfiltration, ultrafiltration and diafiltration.

27. A process for producing soluble amino acids and peptides from a composition comprising insoluble proteins comprising:
    providing an oil seed meal, said oil seed meal being provided by cold pressing at a temperature less than 85° C.;
    mixing the oilseed meal with an aqueous solvent comprising water without any added salt to form a slurry;

if phytic acid is present in the oil seed meal treating the slurry with phytase at a temperature and a pH suitable for phytase activity;

separating the slurry using solid/liquid separation procedures to form:
  a liquid phase, comprising the solvent, soluble protein and oil; and
  a solid phase, comprising residual solvent, insoluble protein and oil washing the solid phase with said aqueous solvent and subjecting the washed solid phase to centrifugation to form:
  a liquid extract; and
  an insoluble protein phase;

dispersing the insoluble protein phase in said aqueous solvent to form an aqueous dispersion of insoluble protein, and adjusting the temperature and pH of the aqueous dispersion to a condition suitable for enzymatic action of one or more of enzymes selected from the group consisting of an endopeptidase, an exopeptidase and a protease, adding a first endopeptidase, exopeptidase or protease enzyme to the temperature and pH adjusted dispersion of insoluble protein, stirring the enzyme-containing dispersion of insoluble protein for a predetermined period of time to form hydrolyzed protein in said dispersion, and subjecting the hydrolyzed protein dispersion to a separation process to obtain a solution of soluble amino acids and peptides wherein the protein isolate comprises at least 90% protein (w/w) on a dry weight basis;
  a solid phase comprising insoluble protein and an oil.

28. The process of claim 27 further including drying the solution of hydrolyzed soluble protein and peptides to obtain a dry soluble protein and peptide composition substantial free of water and oil.

29. The process of claim 27 wherein the oil seed meal comprises a dry, partially defatted pressed cake meal or a wet oily meal having at least about 9% oil.

30. The process according to claim 1, wherein the process further comprises mixing the solid phase with water without any added salt and repeating a solid/liquid separation from one to four times.

31. The process of claim 27, wherein the temperature suitable for endopeptidase, exopeptidase and a protease activity is 60° C. and the suitable pH is about 8.3.

32. The process according to claim 31 wherein the first enzyme is an endopeptidase or exopeptidase and the endopeptidase or exopeptidase is stirred with the dispersion of insoluble protein.

33. The process according to claim 32 wherein the endopeptidase or exopeptidase is stirred with the dispersion of insoluble protein for about 4 hours.

34. The process according to claim 32 wherein, following stirring, the temperature of the enzyme containing slurry is reduced to about 50° C., a second endopeptidase or an exopeptidase or protease is added to the enzyme containing slurry and said slurry is stirred.

35. The process of claim 34 wherein the stirring of the enzyme containing slurry is continued for about an additional four hours.

36. The process according to claim 27, wherein the separation process comprises one or more filtration procedures including one or more of ultrafiltration, nanofiltration and diafiltration.

37. The process according to claim 34, wherein the separation process comprises one or more filtration procedures including one or more of ultrafiltration, nanofiltration and diafiltration.

38. The process according to claim 27 further including contacting the solution of soluble amino acids and peptides with carbon prior to a filtration step.

39. The process of claim 27 wherein the oil seed meal is subjected to a process to remove fiber prior to mixing the oilseed meal with the aqueous solvent to form the slurry.

40. The process of claim 34 wherein the solution of soluble amino acids and peptides is subjected to nanofiltration to obtain a retentate suitable for spray drying.

41. The process according to claim 27, wherein the solution of soluble amino acids and peptides is dried to form dry hydrolysate products having from about 79% to about 95% protein on a dry weight basis.

42. The process of claim 41 wherein the dry hydrolyzates have an amino acid profile as set forth in the following table:

| | Seed Type | | | | |
|---|---|---|---|---|---|
| | Juncea | Juncea | Juncea | Juncea | Napus |
| Amino acid profile (g/100 g product as is) | | | | | |
| Aspartic acid | 7.32 | 6.29 | 6.42 | 6.67 | 6.09 |
| Glutamic acid | 18.1 | 17.1 | 18.2 | 20 | 15.9 |
| Serine | 3.91 | 2.48 | 4.55 | 4.84 | 4.3 |
| Glycine | 4.71 | 4.46 | 4.64 | 4.86 | 4.09 |
| Histidine | 3.45 | 3.63 | 3.5 | 3.47 | 2.55 |
| Arginine | 5.10 | 2.14 | 5.1 | 4.63 | 3.49 |
| Threonine | 3.60 | 3.15 | 3.62 | 3.74 | 3.36 |
| Alanine | 3.99 | 3.86 | 4.08 | 4.49 | 3.71 |
| Proline | 5.52 | 5.52 | 5.5 | 5.29 | 5.43 |
| Tyrosine | 3.16 | 2.20 | 2.96 | 2.78 | 2.97 |
| Valine | 4.87 | 5.01 | 4.27 | 4.51 | 4.22 |
| Methionine | 2.06 | 2.03 | 2.12 | 2.32 | 2.03 |
| Cystine | 2.12 | 2.17 | 2.29 | 2.21 | 2.16 |
| Isoleucine | 4.12 | 4.30 | 3.62 | 3.74 | 3.13 |
| Leucine | 7.07 | 7.09 | 6.82 | 7.27 | 5.96 |
| Phenylalanine | 3.98 | 4.07 | 3.75 | 3.72 | 3.43 |
| Lysine | 5.31 | 4.92 | 4.76 | 5.05 | 4.42 |
| Tryptophan | 1.37 | 1.47 | 1.39 | 0.96 | 1.08 |
| Total Amino Acids | 89.7 | 81.9 | 87.6 | 90.6 | 78.3 |
| Non amino acid material | 10.3 | 18.1 | 12.4 | 9.4 | 21.7 |
| Amino Acid Score | 1.233 | 1.252 | 1.132 | 1.161 | 1.176. |

43. The process of claim 41 wherein the dry hydrolyzates have an amino acid and peptide molecular weight profile as set forth in the following table:

| | Batch # | | | | |
|---|---|---|---|---|---|
| | 1 | 2 | 3a | 3b | 5 |
| Source | Juncea | Juncea | Juncea | Juncea | Napus |
| Enzyme Combination | Alcalase/ Flavourzyme | Alcalase/ Flavourzyme | Alcalase/ Neutrase | Alcalase/ Neutrase | Alcalase/ Neutrase |
| Enzyme 1 Alcalase | 0.5% | 1.5% | 1.5% | 1.5% | 1.5% |

-continued

|  |  | Batch # | | | | |
|---|---|---|---|---|---|---|
|  |  | 1 | 2 | 3a | 3b | 5 |
| Enzyme 2 | | 0.14% Flavourzyme | 0.4% Flavourzyme | 0.2% Neutrase | 0.2% Neutrase 2.5% of solution | 0.2% Neutrase |
| Carbon Treatment | | | | | | |
| Molecular Mass (kDa) | >10 | 0 | 0 | 0 | 0 | 0 |
|  | 10-5 | 0 | 0 | 0 | 0 | 0 |
|  | 3-5 | 0 | 0 | 0 | 0 | 3 |
|  | 0.6-3 | 25 | 16 | 9 | 9 | 10 |
|  | Dimer | 37 | 35 | 62 | 63 | 53 |
|  | Monomer | 36 | 47 | 28 | 26 | 32 |
| Free Tryptophan ($g * 100\ g^{-1}$) | | 0.27 | 0.42 | <0.1 | <0.1 | <0.1. |

44. The process of claim 27 wherein separation process comprises one or more steps of microfiltration, ultrafiltration and diafiltration.

45. The process of claim 27 wherein the endopeptidase or exopeptidase is provided at a concentration of up to about 1.5% of the oil seed meal and the exopeptidase or protease is provided at a concentration up to about 0.4% of the oil seed meal.

46. A process for forming a dry soluble amino acid and peptide mixture from a cold pressed cake of canola meal, said cold pressed cake provided by pressing at a temperature less than 85° C. said pressed cake containing at least about 9% oil, comprising
   a) separating insoluble proteins in said pressed cake from the fiber, soluble proteins, and oil therein,
   b) forming a slurry of the insoluble proteins in a liquid comprising water without any added salt,
   c) adjusting the temperature and pH of said slurry to a condition suitable for enzymatic activity of a first hydrolyzing enzyme, reacting said slurry with said first hydrolyzing enzyme for a preset period of time,
   d) adjusting the temperature and pH of said slurry to a condition suitable for enzymatic activity of a second hydrolyzing enzyme, reacting said slurry with said second hydrolyzing enzyme for a preset period,
   e) the first and second hydrolyzing enzymes reacting with the insoluble proteins to form soluble amino acids and peptides,
   f) separating the soluble amino acids and peptides from residual insoluble materials, and
   g) drying the separated soluble amino acids and peptides wherein the protein isolate comprises at least 90% protein (w/w) on a dry weight basis.

* * * * *